(12) United States Patent
Iida et al.

(10) Patent No.: US 9,647,305 B2
(45) Date of Patent: May 9, 2017

(54) ELECTRODE MATERIAL, ELECTRODE, AND BATTERY

(71) Applicant: Sony Corporation, Tokyo (JP)

(72) Inventors: Hironori Iida, Kanagawa (JP); Kenichi Murata, Kanagawa (JP); Takaaki Nakagawa, Kanagawa (JP); Shinichiro Yamada, Kanagawa (JP)

(73) Assignee: Sony Corporation, Tokyo (JP)

( * ) Notice: Subject to any disclaimer, the term of this patent is extended or adjusted under 35 U.S.C. 154(b) by 186 days.

(21) Appl. No.: 14/167,756

(22) Filed: Jan. 29, 2014

(65) Prior Publication Data

US 2014/0220459 A1 Aug. 7, 2014

(30) Foreign Application Priority Data

Feb. 5, 2013 (JP) ................................. 2013-020215

(51) Int. Cl.
| | |
|---|---|
| *H01M 4/86* | (2006.01) |
| *H01M 12/08* | (2006.01) |
| *H01M 4/90* | (2006.01) |
| *H01M 4/92* | (2006.01) |
| *H01M 4/96* | (2006.01) |
| *H01M 8/16* | (2006.01) |
| *H01M 12/06* | (2006.01) |

(52) U.S. Cl.
CPC ......... *H01M 12/08* (2013.01); *H01M 4/9083* (2013.01); *H01M 4/926* (2013.01); *H01M 4/96* (2013.01); *H01M 8/16* (2013.01); *H01M 12/06* (2013.01); *Y02E 60/527* (2013.01)

(58) Field of Classification Search
CPC ...... H01M 4/9083; H01M 4/926; H01M 4/96; H01M 8/16; H01M 12/06; H01M 12/08; Y02E 60/50; Y02E 60/523
See application file for complete search history.

(56) References Cited

U.S. PATENT DOCUMENTS

| | | | | |
|---|---|---|---|---|
| 2007/0196722 | A1* | 8/2007 | Tomita | H01M 8/04201 429/401 |
| 2010/0291167 | A1* | 11/2010 | Iida | A61K 8/19 424/401 |
| 2011/0180749 | A1* | 7/2011 | Gotou | C01B 31/02 252/182.1 |
| 2012/0286195 | A1* | 11/2012 | Gotou | B01J 20/20 252/73 |
| 2012/0315477 | A1* | 12/2012 | Tashiro | A45D 34/04 428/367 |

FOREIGN PATENT DOCUMENTS

JP 2012-517075 A 7/2012

OTHER PUBLICATIONS

Kenji Kano, "Significance of Carbon Electrode Materials to Improve the Performance of DET-type Fructose/O2 Biofuel cells", Atstract #1437, 221st ECS Meeting, The Electrochemical Society, 2012, 1 page.

* cited by examiner

*Primary Examiner* — Brittany Raymond
(74) *Attorney, Agent, or Firm* — Sheridan Ross P.C.

(57) ABSTRACT

An electrode includes a plant-derived porous carbon material having an ability to catalyze oxygen reduction.

19 Claims, 10 Drawing Sheets

ELECTRODE MATERIAL, ELECTRODE, AND BATTERY

CROSS REFERENCE TO RELATED APPLICATIONS

This application claims the benefit of Japanese Priority Patent Application JP 2013-020215 filed Feb. 5, 2013, the entire contents of which are incorporated herein by reference.

BACKGROUND

The present disclosure relates to an electrode material, an electrode, and a battery.

Electrodes having an ability to catalyze oxygen reduction (hereafter, may be referred to as "oxygen reduction electrode") are used in various types of batteries, electrodes, and sensors such as:

(A) enzymatic biofuel cells that use organic matter such as sugar, alcohol, or cellulose as a fuel;

(B) microbial fuel cells used in wastewater treatment or sludge treatment, in which a reaction is caused using organic matter contained in the wastewater or sludge to decompose the organic matter;

(C) metal-air batteries that include a negative electrode with a negative-electrode-active material including a metal and an alloyed material;

(D) various types of fuel cells such as a polymer electrolyte fuel cell, a phosphoric-acid fuel cell, a molten carbonate fuel cell, a solid-oxide fuel cell, an alkaline fuel cell, and a direct-methanol fuel cell;

(E) gas diffusion electrodes for oxygen reduction used in brine electrolysis; and (F) electrochemical sensors for detecting oxygen.

An existing oxygen reduction catalyst, which constitutes the oxygen reduction electrode, having a remarkable ability to catalyze oxygen reduction is Platinum (Pt). However, because of the high price of platinum, there has been a strong demand for a replacement catalyst for platinum.

A metal-air battery including a negative electrode containing zinc, aluminium, or magnesium and a positive electrode containing at least one oxygen reduction catalyst is known from, for example, Japanese Unexamined Patent Application Publication (Translation of PCT Application) No. 2012-517075. The metal-air battery disclosed in Japanese Unexamined Patent Application Publication (Translation of PCT Application) No. 2012-517075 includes an oxygen reduction catalyst containing a noble metal or the like, and the oxygen reduction catalyst is supported on carbon black, graphite, charcoal, activated carbon, or the like.

SUMMARY

In Japanese Unexamined Patent Application Publication (Translation of PCT Application) No. 2012-517075, carbon black, graphite, charcoal, and activated carbon are referred to as a material on which an oxygen reduction catalyst is supported. However, there is no mention in Japanese Unexamined Patent Application Publication (Translation of PCT Application) No. 2012-517075 that these materials themselves may serve as an oxygen reduction catalyst.

For example, since enzymatic biofuel cells and microbial fuel cells desire a pH-neutral operating condition, their oxygen reduction electrodes (oxygen reduction catalysts) have to exhibit an ability to catalyze oxygen reduction under a pH-neutral condition. However, types of an oxygen reduction catalyst that exhibits the ability to catalyze oxygen reduction under a pH-neutral condition are limited, and the oxygen reduction catalysts disclosed in Japanese Unexamined Patent Application Publication (Translation of PCT Application) No. 2012-517075 have a poor ability to catalyze oxygen reduction under a pH-neutral condition. An existing example of an oxygen reduction catalyst having an ability to catalyze oxygen reduction under a pH-neutral condition is an enzyme "bilirubin oxidase" (see, $221^{st}$ ECS Meeting, 2012 The Electrochemical Society, Abstract #1437, Kano Kenji, "Significance of Carbon Electrode Materials to Improve the Performance of DET-type Fructose/$O_2$ Biofuel cells"). However, a battery using this enzyme has a low electric current density, and the maximum electric current density that has been reported to date is about 40 $mA/cm^2$. In addition, one of the most serious disadvantages of enzymes are their low stability.

Accordingly, it is desirable to provide an electrode material capable of serving under a pH-neutral condition, an electrode including the electrode material, and a battery including the electrode.

According to an embodiment of the present disclosure, there is provided an electrode including a plant-derived porous carbon material having an ability to catalyze oxygen reduction.

According to an embodiment of the present disclosure, there is provided an electrode material including a plant-derived porous carbon material having an ability to catalyze oxygen reduction.

According to an embodiment of the present disclosure, there is provided a battery including a positive electrode including a plant-derived porous carbon material having an ability to catalyze oxygen reduction.

The electrode material, the electrode, and the positive electrode of the battery according to the embodiment of the present disclosure include a plant-derived porous carbon material having an ability to catalyze oxygen reduction and therefore sufficiently exhibit an oxygen reduction ability under a pH-neutral condition. Furthermore, since the electrode material, the electrode, and the positive electrode of the battery according to the embodiment of the present disclosure do not use enzymes, there are fewer limitations on the operating environment of the electrode and battery, which depends on the structure of the battery.

DETAILED DESCRIPTION OF EMBODIMENTS

Figure 1:
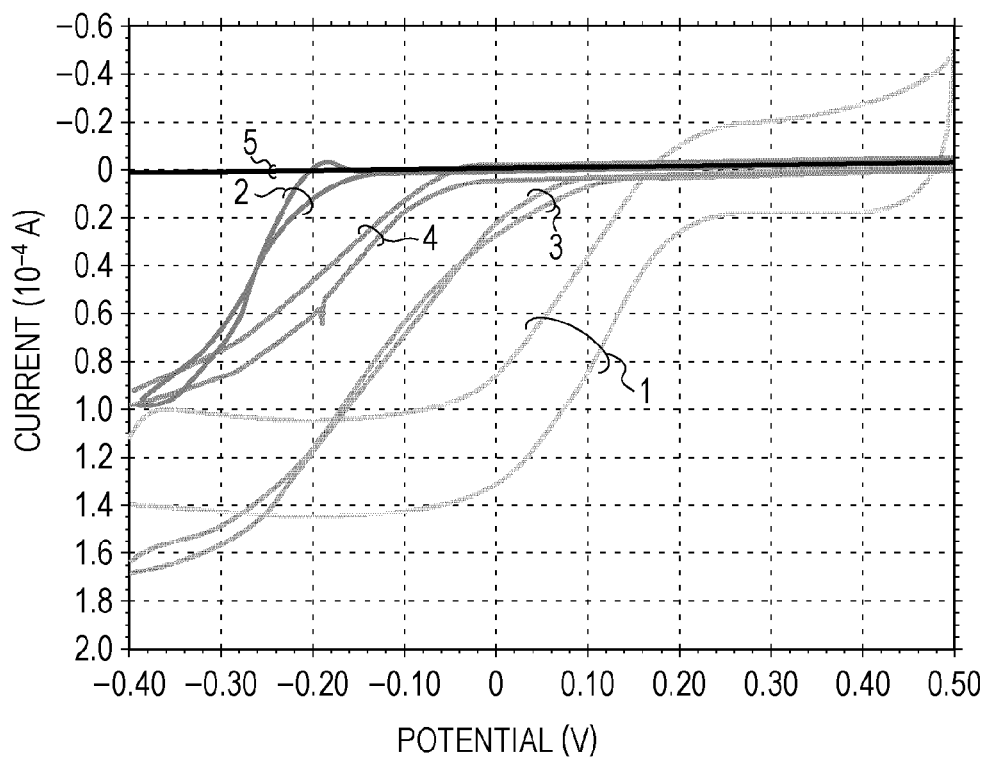
FIG. 1 is a graph showing the results of evaluation of the oxygen reduction abilities of test oxygen reduction electrodes prepared in Example 1 and Comparative Examples 1A to 1D.

Hereafter, the present disclosure is described on the basis of the following examples with reference to the attached drawings. However, the present disclosure is not limited to these examples. Various values and materials used in these examples are illustrative. The description will be given in the following order:

1. General description of an electrode material, an electrode, and a battery according to an embodiment of the present disclosure 2. Example 1 (an electrode material and an electrode according to an embodiment of the present disclosure)

3. Example 2 (variations of the electrode material and the electrode prepared in Example 1)

4. Example 3 (a battery according to an embodiment of the present disclosure)

5. Example 4 (variations of the battery prepared in Example 3), etc.

[General Description of an Electrode Material, an Electrode, and a Battery According to an Embodiment of the Present Disclosure]

In an electrode material, an electrode, and a battery according to an embodiment of the present disclosure (hereafter, these may be collectively referred to as "an embodiment of the present disclosure"), a porous carbon material may be used for oxygen reduction at a pH of 3 or more and 10 or less. Specifically, a porous carbon material may be used for oxygen reduction in an electrolyte having a pH of 3 or more and 10 or less.

According to an embodiment of the present disclosure including the preferred embodiment described above, the specific surface area of the porous carbon material may be 100 m$^2$/g or more as measured by the nitrogen BET method and the pore volume of the porous carbon material may be 0.2 cm$^3$/g or more as measured by the BJH method and 0.1 cm$^3$/g or more as measured by the MP method.

According to an embodiment of the present disclosure including the preferred embodiments described above, the oxygen reduction starting potential of the porous carbon material (i.e., electrode material, electrode, or positive electrode) may be more noble than 0.15 V as measured versus a Ag/AgCl reference electrode.

A battery according to an embodiment of the present disclosure including the preferred embodiments described above may include an electrolytic solution having a pH of 3 or more and 10 or less. In order to maintain the pH of 3 or more and 10 or less, for example, the electrolytic solution may contain a buffer substance. Generally, any buffer substance may be used as long as it has a pK$_a$ of 4 or more and 10 or less. The content of the buffer substance is preferably 0.2 mol or more per liter of the electrolytic solution. The maximum content of the buffer substance in the electrolytic solution may be, for example, the maximum solubility of the buffer substance in the electrolytic solution. More preferably, the content of the buffer substance in the electrolytic solution may be close to the maximum solubility of the buffer substance in the electrolytic solution.

In an electrode and a battery according to an embodiment of the present disclosure including the preferred embodiments described above, the porous carbon material may include an oxygen reduction catalyst supported on the porous carbon material. The oxygen reduction catalyst may be at least one material selected from the group consisting of noble metals including platinum (Pt), transition-metal oxides, organometallic complexes and polymers thereof (specifically, e.g., a transition-metal porphyrin, phthalocyanine, a porphyrin polymer produced by polymerization of transition-metal porphyrins, and a phthalocyanine polymer produced by polymerization of phthalocyanines), perovskite, and a product of pyrolysis of a cobalt salt using polyacrylonitrile. Other examples of the oxygen reduction catalyst include LaBO$_3$ (B: Mn, Co) perovskite-type oxides, nitrides, and sulfides; and multi-component perovskite oxides such as La$_{1-x}$A'$_x$Co$_{1-y}$Fe$_y$O$_3$ (where A' represents Sr or Ca, and x and y are 0.2 to 0.5). These oxygen reduction catalysts are used for four-electron reduction of oxygen.

In an electrode and a battery according to an embodiment of the present disclosure including the preferred embodiments described above, the porous carbon material may be supported on a supporting member. An electrode according to an embodiment of the present disclosure including the preferred embodiments described above may be used as the positive electrode of a battery.

A specific method for measuring the oxygen reduction starting potential of the porous carbon material (i.e., electrode material) is described below. A test oxygen reduction electrode is prepared by forming a film on a commercially-available grassy-carbon electrode (specifically, grassy-carbon electrode produced by BAS Inc.) by depositing a paste prepared from a plant-derived porous carbon material. Then, the oxygen reduction ability of the test oxygen reduction electrode is evaluated by an electrochemical measurement while the test oxygen reduction electrode is rotated at 1,000 rmp in an air-saturated phosphate buffer (pH of 7, 1 mol/l) in order to supply the test oxygen reduction electrode with oxygen. The measurement apparatuses are a rotating disk electrode system RDE-2 and an electrochemical analyzer ALS 701 produced by ALS Co., Ltd. The oxygen reduction starting potential of an electrode or a positive electrode prepared from the porous carbon material may be measured by linear sweep voltammetry using a rotating disk electrode system RDE-2 and an electrochemical analyzer ALS 701. Specifically, a potential at which the oxygen reduction current increases is measured.

According to an embodiment of the present disclosure, the porous carbon material is made from a plant-derived material. Examples of the plant-derived material include, but are not limited to, chaff and straw of rice, barley, wheat, rye, Japanese barnyard millet, foxtail millet, and the like; coffee beans; tea leaves (e.g., green tea leaves and black tea leaves); sugarcanes (specifically, bagasse); maize (specifically, corn cob); fruit peels (e.g., citrus fruit peels such as orange peels, grapefruit peels, and Japanese mandarin peels and banana peels); reeds; and wakame stems. In addition, vascular plants living on land, pteridophytes, bryophytes, algae, seaweeds, and the like may be used. These materials may be used, as the raw material of the porous carbon material, alone or in a mixture of two or more types of these materials. The shape and form of the plant-derived material are not particularly limited. For example, the plant-derived material such as chaff or straw may be used without being processed or in the form of a dried product. Alternatively, the plant-derived material subjected to various processes such as fermentation, roasting, and extraction in processing for manufacturing a beverage such as beer, Western liquor, and the like may be used. In particular, straw and chaff that have been processed by threshing or the like are preferably used in order to recycle industrial waste. These straw and chaff that have been processed by threshing or the like are easily available in large amounts from an agricultural cooperative, an alcoholic beverage manufacturing company, a food company, a food-processing company, or the like.

The silicon (Si) content of a porous carbon material prepared by being treated with an acid or an alkali after carbonization is less than 5% by mass, preferably 3% by mass or less, and more preferably 1% by mass or less. The silicon (Si) content of the raw material (i.e., a plant-derived material before carbonization) is preferably 5% by mass or more.

The porous carbon material according to an embodiment of the present disclosure may be prepared by, for example, carbonizing a plant-derived material at 400° C. to 1,400° C. and subsequently treating the carbonized material with an acid or an alkali. In a method for producing the porous carbon material according to an embodiment of the present disclosure (hereafter, may be referred to as "method for producing the porous carbon material"), a material that is prepared by carbonizing a plant-derived material at 400° C. to 1,400° C. and that has not yet been treated with an acid or an alkali is referred to as "precursor of a porous carbon material" or "carbonaceous substance".

In the method for producing the porous carbon material, an activation treatment may be performed after the acid or alkali treatment. The activation treatment may be performed before the acid or alkali treatment. In the method for producing the porous carbon material including the preferred method described above, depending on the type of the plant-derived material used, before being carbonized, the plant-derived material may be subjected to a heat treatment (preliminary carbonization treatment) at a temperature (e.g., 400° C. to 700° C.) lower than the temperature for carbonization under exclusion of oxygen. This allows a tar component that is considered to be produced through carbonization to be extracted, which results in a reduction in the amount of tar component produced or removal of the tar component produced. A condition where oxygen is excluded may be achieved by preparing an atmosphere of an inert gas such as nitrogen gas or argon gas or a vacuum atmosphere or by "smothering" a plant-derived material. In the method for producing the porous carbon material, depending on the type of the plant-derived material used, the plant-derived material may be immersed in an alcohol (e.g., methyl alcohol, ethyl alcohol, or isopropyl alcohol) in order to reduce the contents of mineral components and moisture in the plant-derived material and to prevent an offensive smell from being given off in the carbonization. In the method for producing the porous carbon material, the preliminary carbonization treatment may be performed after the immersion treatment with an alcohol. Examples of a material that is preferably heat-treated in an inert gas include plants that yield a large amount of pyroligneous acid (tar and light-oil components). Examples of a material that is preferably subjected to the preliminary treatment with an alcohol include sea weeds, which contain iodine and various minerals in abundance.

In the method for producing the porous carbon material, a plant-derived material is carbonized at 400° C. to 1,400° C. The term "carbonization" generally refers to converting an organic substance (i.e., plant-derived material for the porous carbon material according to an embodiment of the present disclosure) into a carbonaceous substance by a heat treatment (e.g., see JIS M0104-1984). An example of an atmosphere used for carbonization is an atmosphere from which oxygen has been excluded. Specific examples thereof include a vacuum atmosphere, an atmosphere of an inert gas such as nitrogen gas or argon gas, and an atmosphere in which a plant-derived material is "smothered". The rate of temperature rise until the carbonization temperature is achieved is, but not limited to, 1° C./min or more, preferably 3° C./min or more, and more preferably 5° C./min or more in the above-described atmosphere. The maximum carbonization duration is, for example, but not limited to, 10 hours, preferably 7 hours, and more preferably 5 hours. The minimum carbonization duration may be set to a time in which a plant-derived material is fully carbonized. A plant-derived material may be pulverized, if necessary, to a desired grain size or may be classified. The plant-derived material may be washed in advance. Alternatively, after a precursor of a porous carbon material or a porous carbon material is prepared, it may be pulverized, if necessary, to a desired grain size or may be classified. In another case, after a porous carbon material is subjected to the activation treatment, it may be pulverized, if necessary, to a desired grain size or may be classified. The finally produced porous carbon material may be subjected to a sterilization treatment. The type, components, and structure of a furnace used for carbonization are not limited, and both a continuous-type furnace and a batch-type furnace may be used.

In the method for producing the porous carbon material, as described above, the number of micropores having a diameter smaller than 2 nm may be increased by the activation treatment. Examples of the activation treatment method include a gas-activation method and a chemical-activation method. The gas-activation method herein refers to a method in which a porous carbon material is heated for several ten minutes to several hours at 700° C. to 1,400° C., preferably 700° C. to 1,000° C., and more preferably 800° C. to 1,000° C. in a gas atmosphere using oxygen, water vapor, carbonic acid gas, air, or the like as an activator to promote development of the microstructure of the volatile components and carbon molecules in the porous carbon material. More specifically, the heating temperature may be selected appropriately on the basis of the type of the plant-derived material used, the type and concentration of the gas used, and the like. The chemical-activation method herein refers to a method in which a porous carbon material is activated using zinc chloride, iron chloride, calcium phosphate, calcium hydroxide, magnesium carbonate, potassium carbonate, sulfuric acid, or the like instead of oxygen, water vapor, or the like used in the gas-activation method, washed with hydrochloric acid, added in an alkaline aqueous solution to adjust the pH of the porous carbon material, and then dried.

In the method for producing the porous carbon material, silicon components in the carbonized plant-derived material are removed by an acid or alkali treatment. Examples of the silicon components include silicon oxides such as silicon dioxide, silicon oxide, and silicates. A porous carbon material having a large specific surface area may be produced by removing these silicon components in the carbonized plant-derived material. In some cases, alternatively, the silicon components in the carbonized plant-derived material can be removed by a dry-etching method.

The porous carbon material according to an embodiment of the present disclosure includes a large number of pores, which are classified as "mesopores" having a diameter of 2 to 50 nm, "macropores" having a diameter of more than 50 nm, and "micropores" having a diameter of less than 2 nm. Specifically, the diameter of mesopores included in the porous carbon material in large numbers is, for example, 20 nm or less and particularly 10 nm or less. The diameters of micropores included in the porous carbon material in large numbers are, for example, about 1.9 nm, about 1.5 nm, and about 0.8 to 1 nm. The pore volume of the porous carbon material according to an embodiment of the present disclosure is 0.2 cm$^3$/g or more, preferably 0.3 cm$^3$/g or more, and more preferably 0.5 cm$^3$/g or more as measured by the BJH method. The pore volume of the porous carbon material according to an embodiment of the present disclosure is 0.1 cm$^3$/g or more, preferably 0.2 cm$^3$/g or more, more preferably 0.3 cm$^3$/g or more, and further preferably 0.5 cm$^3$/g or more as measured by the MP method.

The specific surface area of the porous carbon material according to an embodiment of the present disclosure (hereafter, may be referred to simply as "specific surface area") is preferably 400 m$^2$/g or more as measured by the nitrogen BET method in order to impart a better functionality to the porous carbon material.

The nitrogen BET method is a method in which adsorbing molecules (herein, nitrogen molecules) are adsorbed to and desorbed from an absorbent (herein, porous carbon material) to determine an adsorption isotherm, and the adsorption isotherm is then analyzed by the BET equation represented by Equation (1). The specific surface area and pore volume may be calculated by this method. A specific method for calculating the specific surface area by the nitrogen BET method is described below. Nitrogen molecules serving as adsorbing molecules are adsorbed to and desorbed from a porous carbon material to determine an adsorption isotherm. Then, $[p/\{V_a(p_0-p)\}]$ is calculated from the adsorption isotherm by Equation (1) or Equation (1'), which is a deformation of Equation (1), and plotted against the relative equilibrium pressure ($p/p_0$). The resulting plotted line is considered to be a straight line, and the slope s $(=[(C-1)/(C \times V_m)])$ and the intercept i $(=[1/(C \times V_m)])$ of the straight line are calculated by a least-squares method. $V_m$ and C are calculated from the slope s and the intercept i by Equations (2-1) and (2-2), respectively. Then, the specific surface area $a_{sBET}$ is calculated from $V_m$ by Equation (3) (see the manual for BELSORP-mini and BELSORP analysis software produced by BEL Japan, Inc., pp. 62-66). The nitrogen BET method is a measurement method conforming to JIS R 1626-1996 "measuring methods for the specific surface area of fine ceramic powders by gas adsorption using the BET method".

$$V_a=(V_m \times C \times p)/[(p_0-p)\{1+(C-1)(p/p_0)\}] \qquad (1)$$

$$[p/\{V_a(p_0-p)\}]=[(C-1)/(C \times V_m)](p/p_0)+[1/(C \times V_m)] \qquad (1')$$

$$V_m=1/(s+i) \qquad (2-1)$$

$$C=(s/i)+1 \qquad (2-2)$$

$$a_{sBET}=(V_m \times L \times \sigma)/22414 \qquad (3)$$

(where $V_a$ represents the volume of nitrogen adsorbed; $V_m$ represents the volume of nitrogen adsorbed on a monomolecular layer; p represents the equilibrium pressure of nitrogen; $p_0$ represents the saturated vapor pressure of nitrogen; L represents the Avogadro's number; and $\sigma$ represents the adsorption cross section of nitrogen)

In order to calculate the pore volume $V_p$ by the nitrogen BET method, for example, adsorption data of the adsorption isotherm are linearly interpolated, and an adsorption volume V at the relative pressure set for calculating the pore volume is determined. The pore volume $V_p$ can be calculated from the adsorption volume V by Equation (4) (see the manual for BELSORP-mini and BELSORP analysis software produced by BEL Japan, Inc., pp. 62-65). Hereafter, a pore volume determined by the nitrogen BET method may be simply referred to as "pore volume".

$$V_p=(V/22414) \times (M_g/\rho_g) \qquad (4)$$

(where V represents the volume of nitrogen adsorbed at the relative pressure; $M_g$ represents the molecular weight of nitrogen; and $\rho_g$ represents the density of nitrogen)

The diameter of mesopores can be calculated as pore distribution from the rate of change in the pore volume relative to the pore diameter by the BJH method or the like. The BJH method is a method that is widely used as a method for analyzing pore distribution. The pore distribution can be analyzed by the BJH method as follows. Nitrogen molecules serving as adsorbing molecules are adsorbed on and desorbed from a porous carbon material to determine an adsorption isotherm. Then, the thickness of an adsorption layer created when the adsorbing molecules (e.g., nitrogen molecules) are gradually adsorbed on and desorbed from pores filled with the adsorption molecules and the inner diameter (twice as long as the core radius) of pores created at that time are determined from the adsorption isotherm. The pore radius $r_p$ is calculated by Equation (5), and the pore volume is calculated by Equation (6). The rate $(dV_p/dr_p)$ of change of the pore volume is plotted against the pore diameter ($2r_p$), which are calculated from the pore radius and the pore volume, to draw a pore distribution curve (see the manual for BELSORP-mini and BELSORP analysis software produced by BEL Japan, Inc., pp. 85-88).

$$r_p=t+r_k \qquad (5)$$

$$V_{pn}=R_n \times dV_n - R_n \times dt_n \times c \times \Sigma A_{pj} \qquad (6)$$

where, $$R_n=r_{pn}^2/(r_{kn-1}+dt_n)^2 \qquad (7)$$

(where $r_p$ represents the pore radius; $r_k$ represents the core radius ((inner diameter)/2) when an adsorption layer having a thickness t is adsorbed on the inner wall of a pore having a radius $r_p$ at the pressure; $V_{pn}$ represents the pore volume at adsorption and desorption of nitrogen in the n-th time; $dV_n$ represents the amount of change in volume at that time; $dt_n$ represents the amount of change in the thickness $t_n$ of the adsorption layer at adsorption and desorption of nitrogen in the n-th time; $r_{kn}$ represents the core radius at that time; c is a fixed value; $r_{pn}$ represents the pore radius at adsorption and desorption of nitrogen in the n-th time; and $\Sigma A_{pj}$ represents an integrated value of the areas of the wall surfaces of the pores from j=1 to j=n−1)

The diameter of micropores may be calculated, for example, as a pore distribution from the rate of change in the pore volume relative to the pore diameter in accordance with the MP method. When pore distribution is analyzed by the MP method, nitrogen molecules are adsorbed on and desorbed from a porous carbon material, and thereby an adsorption isotherm is determined. The adsorption isotherm is converted (t-plot) into a curve showing pore volumes plotted against the thickness t of an adsorption layer. A pore distribution curve can be determined on the basis of the curvature of the curve (amount of change in pore volume relative to the amount of change in the thickness t of an adsorption layer) (see the manual for BELSORP-mini and BELSORP analysis software produced by BEL Japan, Inc., pp. 72-73 and p. 82).

Specific examples of a method for treating the precursor of a porous carbon material with an acid or an alkali include a method in which the precursor of a porous carbon material is immersed in an aqueous solution of an acid or an alkali and a method in which the precursor of a porous carbon material is caused to react with an acid or an alkali in a gas phase. More specifically, examples of an acid used for the treatment include acidic fluorine compounds such as hydrogen fluoride, hydrofluoric acid, ammonium fluoride, calcium fluoride, and sodium fluoride. When a fluorine compound is used, the amount of fluorine is preferably four times the amount of silicon contained in silicon components included in the precursor of a porous carbon material. The concentration of an aqueous solution of the fluorine compound is preferably 10% by mass or more. When hydrofluoric acid is used to remove the silicon components (e.g., silicon dioxide) included in the precursor of a porous carbon material, silicon dioxide reacts with hydrofluoric acid as shown by Chemical Formula (A) or (B) and then removed as hydrogen hexafluorosilicate ($H_2SiF_6$) or silicon tetrafluoride ($SiF_4$), and thus a porous carbon material is produced. Subsequently, the porous carbon material may be washed and then dried.

$$SiO_2 + 6HF \rightarrow H_2SiF_6 + 2H_2O \quad (A)$$

$$SiO_2 + 4HF \rightarrow SiF_4 + 2H_2O \quad (B)$$

An example of an alkali used for the treatment is sodium hydroxide. When an aqueous solution of an alkali is used, the pH of the aqueous solution may be 11 or more. When an aqueous sodium hydroxide solution is used to remove the silicon components (e.g., silicon dioxide) included in the precursor of a porous carbon material, silicon dioxide is caused to react as shown by Chemical Formula (C) by heating the aqueous sodium hydroxide solution and then removed as sodium silicate ($Na_2SiO_3$). Thus, a porous carbon material is produced. When the precursor is treated by reacting with sodium hydroxide in a gas phase, solid sodium hydroxide is caused to react as shown by Chemical Formula (C) by being heated and then removed as sodium silicate ($Na_2SiO_3$). Thus, a porous carbon material is produced. Subsequently, the porous carbon material may be washed and dried.

$$SiO_2 + 2NaOH \rightarrow Na_2SiO_2 + H_2O \quad (C)$$

The porous carbon material according to an embodiment of the present disclosure may be, for example, a porous carbon material including pores having three-dimensional periodicity (porous carbon material having an "inverse-opal structure") disclosed in Japanese Unexamined Patent Application Publication No. 2010-106007. Specifically, the porous carbon material includes three-dimensionally arranged spherical pores with an average diameter of $1 \times 10^{-9}$ to $1 \times 10^{-5}$ m and has a surface area of $3 \times 10^2$ $m^2/g$ or more. Preferably, the pores are arranged in the surface of the porous carbon material so as to correspond a crystalline structure or so as to correspond to the arrangement of atoms on the (111) plane of a face-centered cubic structure from a macroscopic point of view.

Examples of the supporting member on which the porous carbon material is supported include woven fabric and unwoven fabric made from various natural fiber or synthetic fiber; carbon/graphite-fiber-containing cloth and carbon/graphite-fiber-based cloth; a sheet-like material produced from carbon fiber; and a foil-like material, a plate-like material, and mesh-like material that are composed of a metal or an alloy. Examples of the metal and the alloy include titanium, an titanium alloy, aluminium, an aluminium alloy, nickel, a nickel alloy, iron, and stainless steel. The porous carbon material may be supported on the supporting member by, for example, preparing a paste containing the porous carbon material, depositing the paste on one surface or both surfaces of the supporting member by spraying, brush coating, printing, painting, spin coating, or the like to form a porous-carbon-material layer composed of the paste, and then drying the porous-carbon-material layer. The amount of porous carbon material supported on the supporting member may be, for example, 0.05 to 5 mg per square centimeter of the surface of the supporting member. The overall thickness of the supporting member including the porous carbon material supported thereon may be, for example, 10 μm to 1 mm.

Examples of the battery according to an embodiment of the present disclosure or a battery in which the electrode material or the electrode according to an embodiment of the present disclosure may be utilized include the following:

(A) enzymatic biofuel cells that use organic matter such as sugar, alcohol, or cellulose as a fuel;

(B) microbial fuel cells used in wastewater treatment or sludge treatment, in which a reaction is caused using organic matter contained in the wastewater or sludge to decompose the organic matter (In microbial fuel cells, microorganisms are used as the negative electrode and the electrode material according to an embodiment of the present disclosure may be used as the positive electrode. Energy produced by microbial decomposition of wastewater or sludge is extracted as electrical energy);

(C) metal-air batteries that include a negative electrode with a negative-electrode-active material including a metal and an alloyed material (Examples of the metal and the alloyed material used as the negative-electrode-active material include alkali metals such as lithium, sodium, and potassium; Group 2 elements such as magnesium and calcium; Group 13 elements such as aluminium; transition metals such as zinc and iron; and alloyed materials and compounds including any of these metals);

(D) various types of fuel cells such as
  (i) a polymer electrolyte fuel cell (PEFC) that includes a fuel electrode (negative electrode), a solid polymer membrane (electrolyte), and an air electrode (positive electrode, which may be the electrode according to an embodiment of the present disclosure) that are merged together to form a membrane-electrode assembly (MEA) interposed between conductive plates called "bipolar plates" in which reaction-gas-feeding passages are formed, (ii) a phosphoric-acid fuel cell (PAFC) that includes a separator impregnated with an electrolyte that is an aqueous phosphoric acid ($H_3PO_4$) solution, (iii) a molten carbonate fuel cell (MCFC) that uses carbonate ions ($CO_3^{2-}$) instead of hydrogen ions ($H^+$) and includes a separator impregnated with an electrolyte that is a molten carbonate (e.g., lithium carbonate or potassium carbonate), (iv) a solid-oxide fuel cell (SOFC) that includes, as an electrolyte, stabilized zirconia having a high oxide-ion permeability or an ion-conducting ceramic such as a perovskite oxide of lanthanum or gallium and that allows oxide ions ($O^{2-}$) produced at the air electrode (positive electrode that is the electrode according to an embodiment of the present disclosure) to pass through the electrolyte and to react with hydrogen or carbon monoxide at the fuel electrode to produce an electrical energy, (v) an alkaline fuel cell (AFC) that includes an ion-conductor that is a hydroxide ion and a separator impregnated with an alkaline electrolytic solution, the separator being interposed between electrodes, and (vi) a direct-methanol fuel cell (DMFC) such as a direct-methanol fuel cell that includes a positive electrode that is the electrode according to an embodiment of the present disclosure and a fuel electrode (negative electrode) at which methanol is directly oxidized;

as applications of the electrode material or the electrode according to an embodiment of the present disclosure, (E) gas diffusion electrodes for oxygen reduction used in brine electrolysis; and (F) electrochemical sensors for detecting oxygen.

The above-described batteries, electrodes, and sensors may include existing components and have an existing structure.

The battery according to an embodiment of the present disclosure may be incorporated into an electronic device. Generally, the type of the electronic device is not limited and may be portable or stationary. Specific examples of the electronic devices include a cellular telephone, a mobile device, a robot, a personal computer, a game machine, a camera-integrated video tape recorder (VTR), a vehicle-mounted device, various home-electric appliances, and industrial goods.

EXAMPLES

Example 1

Example 1 relates to an electrode material according to an embodiment of the present disclosure. The electrode material prepared in Example 1 includes a plant-derived porous carbon material having an ability to catalyze oxygen reduction.

In Example 1 and Examples 2 to 4 described below, the following plant-derived porous carbon material was used. Specifically, a plant-derived material, that is, the raw material of the porous carbon material, was rice chaff. The raw material, that is, chaff was carbonized to be converted into a carbonaceous substance (precursor of the porous carbon material). Then, the carbonaceous substance was treated with an acid to prepare the porous carbon material.

In order to prepare the porous carbon material, the plant-derived material was carbonized at 400° C. to 1,400° C. and the resulting material was treated with an acid or alkali. Specifically, chaff was carbonized (fired) in a nitrogen gas atmosphere at 800° C. to prepare a precursor of the porous carbon material. Then, the precursor of the porous carbon material was treated with an alkali by being immersed in an aqueous sodium hydroxide solution (20 mass %) at 80° C. overnight to remove silicon components in the carbonized plant-derived material, washed with water and ethyl alcohol until the pH of 7 is achieved, and then dried to prepare an intermediate of the porous carbon material. The intermediate of the porous carbon material was heated to 900° C. in a nitrogen gas atmosphere and thereby subjected to an activation treatment with water vapor. The resulting material was pulverized to a size of 4 μm with a jet mill. Thus, the plant-derived porous carbon material of Example 1 was prepared.

In Example 1, 0.1 g of the plant-derived porous carbon material, 250 μl of 10% Nafion (registered trademark), and 5 ml of 2-propanol were mixed to prepare a paste. Nafion, which served as a binder in Example 1, is a product of Sigma-Aldrich Japan K.K. Nafion is a perfluorocarbon material including a hydrophobic Teflon skeleton composed of carbon-fluorine bonds and a perfluoro side chain having a sulfonic group, that is, a copolymer of tetrafluoroethylene and a perfluoro[2-(fluorosulfonylethoxy)propylvinyl ether]. The paste was deposited on the commercially-available glassy carbon electrode described above to form a film. Thus, a test oxygen reduction electrode was prepared. Then, the oxygen reduction ability of the test oxygen reduction electrode was evaluated by an electrochemical measurement while the test oxygen reduction electrode was rotated in an air-saturated phosphate buffer (pH of 7, 1 mol/l) in order to supply the test oxygen reduction electrode with oxygen. The measurement apparatus used were a rotating disk electrode system RDE-2 and an electrochemical analyzer ALS 701 produced by ALS Co., Ltd.

Test oxygen reduction electrodes for Comparative Examples were prepared using the following materials instead of the porous carbon material and evaluated on their oxygen reduction abilities. In addition, as a reference example, the oxygen reduction ability of a platinum electrode was evaluated.

Comparative Example 1A: Vapor-Grown Carbon Fiber "VGCF-H"® Produced by Showa Denko K.K.

Comparative Example 1B: Nitrogen-Doped Carbon Nanotube (Nitrogen Content: 2.5 Mass %) Produced by NANO-MIR CO. LTD.

Comparative Example 1C: High-Surface-Area Graphitized Mesoporous Carbon Produced by Sigma-Aldrich Japan K.K. (Product No. 699624)

Comparative Example 1D: Mesoporous Carbon Produced by Sigma-Aldrich Japan K.K. (Product No. 402110)

Figure 2:
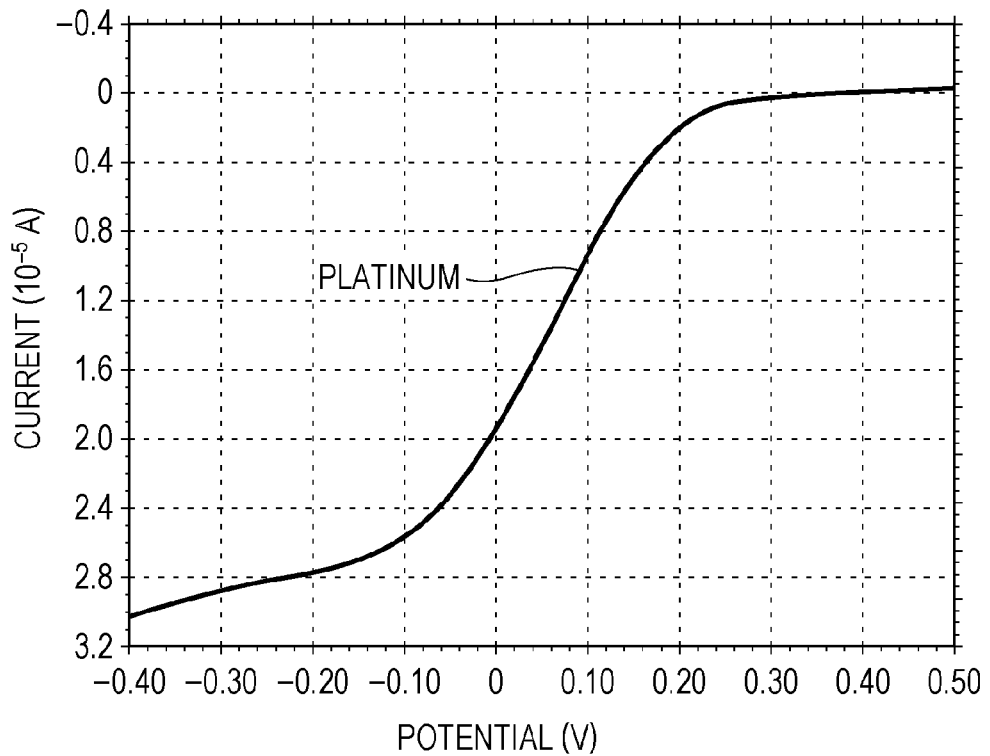
FIG. 2 is a graph showing the results of evaluation of the oxygen reduction ability of a platinum electrode, which is shown as a reference example.

FIGS. 1 and 2 show the measurement results. In FIGS. 1 and 2, the horizontal axis represents voltage (units: V) and the vertical axis represents current (units: $10^{-4}$ A in FIG. 1 and $10^{-5}$ A in FIG. 2). In FIG. 1, the line numbered "1" shows the data of Example 1, the line numbered "2" shows the data of Comparative Example 1A, the line numbered "3" shows the data of Comparative Example 1B, the line numbered "4" shows the data of Comparative Example 1C, and the line numbered "5" shows the data of Comparative Example 1D. FIG. 2 shows the result of evaluation of the oxygen reduction ability of the platinum electrode as a reference example. The comparison of the results shown in FIGS. 1 and 2 shows that the electrode material of Example 1 which included the plant-derived porous carbon material had a catalytic ability (ability to catalyze oxygen reduction) comparable to that of the platinum electrode under a pH-neutral condition (in Example 1, pH of 7) because the oxygen reduction starting potentials of the electrode material of Example 1 was substantially equal to that of the platinum electrode. In other words, the electrode material of Example 1 which included the plant-derived porous carbon material had an overvoltage substantially equal to that of the platinum electrode under a pH-neutral condition. Thus, in the electrode material of Example 1 which included the plant-derived porous carbon material, that is, in an electrode prepared using the electrode material or in an electrode of a battery including such an electrode, the oxygen reduction starting potential of the porous carbon material (i.e., electrode material, electrode, or positive electrode) was more noble than 0.15 V as measured versus a Ag/AgCl reference electrode. FIG. 1 shows that the electrode material of Example 1 which included the plant-derived porous carbon material produced a larger current output than the electrode materials of Comparative Example 1A, Comparative Example 1C, and Comparative Example 1D and had a higher oxygen reduction starting potential than the electrode materials of Comparative Example 1A, Comparative Example 1B, Comparative Example 1C, and Comparative Example 1D. Thus, it is confirmed that the electrode material of Example 1 had a markedly higher performance than the electrode materials of Comparative Examples.

Figure 3A:
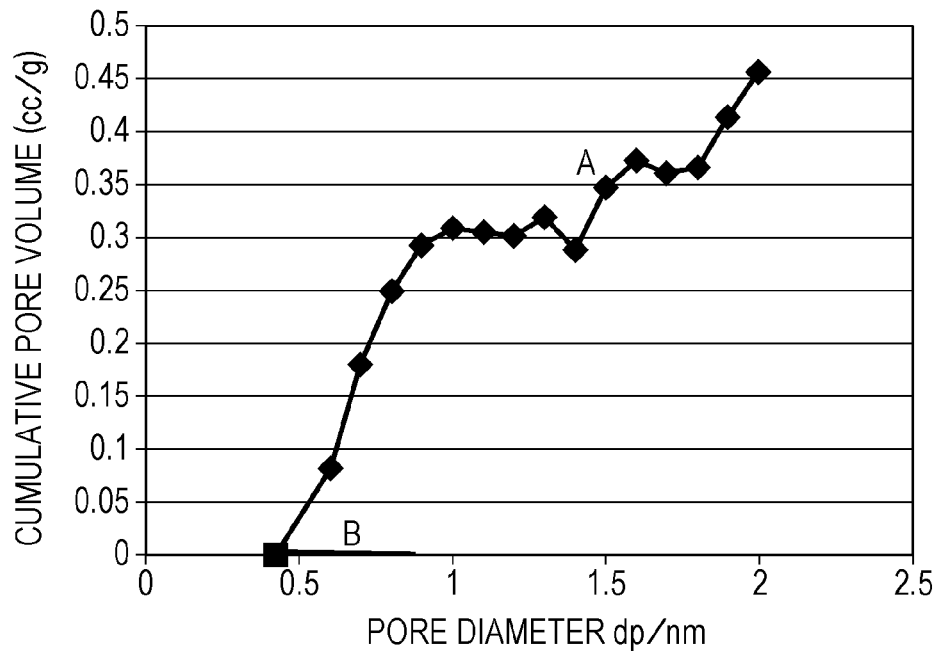
FIGS. 3A and 3B each show the results of measurement of the cumulative pore volumes of a plant-derived porous carbon material used in Example 1 and a material used in Comparative Example 1A.
Figure 3B:
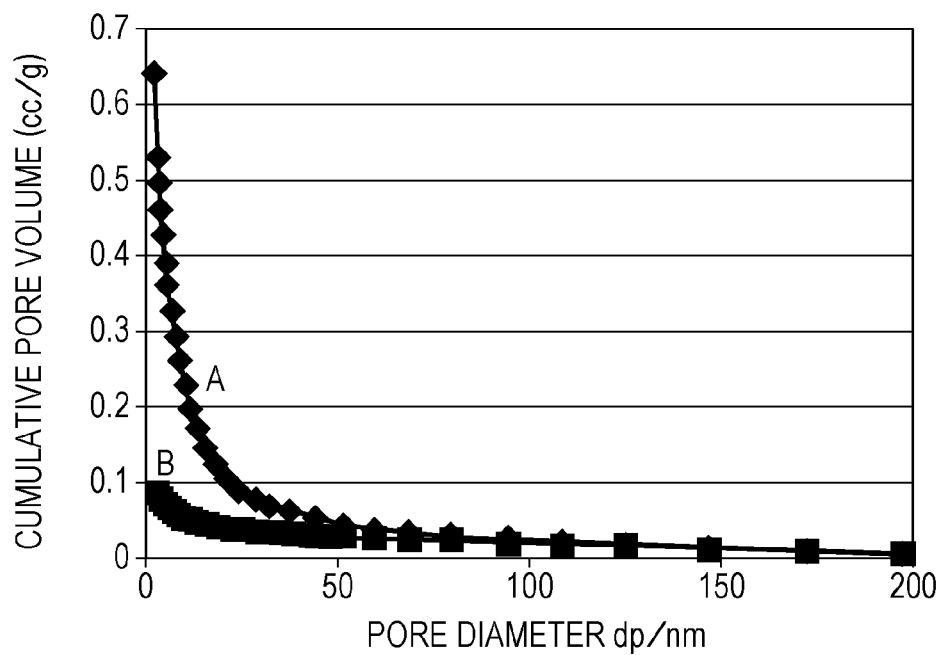

Table 1 shows the specific surface areas of the plant-derived porous carbon material of Example 1 and the material used in Comparative Example 1A as measured by the nitrogen BET method ("specific surface area" in Table 1, units: $m^2/g$), the pore volume of these materials as measured by the nitrogen BET method ("volume by BET method" in Table 1, units: $cm^3/g$), the pore volume as measured by the MP method ("MP method" in Table 1, units: $cm^3/g$), and the pore volume as measured by the BJH method ("BJH method" in Table 1, units: $cm^3/g$). FIGS. 3A and 3B show the measurement results of the cumulative pore volume. In FIGS. 3A and 3B, the plotted curve denoted by "A" shows the data of Example 1 and the plotted curve denoted by "B" shows the data of Example 2. The measurement result of a sample having a significantly small specific surface area, such as the sample of Comparative Example 1A, shows the behavior shown by "B" in FIG. 3A. In reality, negative values were observed and therefore the plotted line is invisible.

TABLE 1

| | Specific surface area | Volume by BET method | MP method | BJH method |
|---|---|---|---|---|
| Example 1 | 1220 | 0.998 | 0.456 | 0.642 |
| Comparative Example 1A | 13 | 0.081 | 0.0 | 0.087 |

The results shown in Table 1 show that the plant-derived porous carbon material of Example 1 had a pore structure quite different from that of the material used in Comparative Example 1A. Specifically, the plant-derived porous carbon material of Example 1 had a specific surface area of 100 $m^2/g$ or more as measured by the nitrogen BET method, a pore volume of 0.2 $cm^3/g$ or more as measured by the BJH method, and a pore volume of 0.1 $cm^3/g$ or more as measured by the MP method. Thus, the electrode material of Example 1 sufficiently exhibited an oxygen reduction ability under a pH-neutral condition and produced a large current output presumably because of this unique pore structure of the plant-derived porous carbon material.

As described above, an electrode material having a remarkable ability to catalyze oxygen reduction may be produced by preparing the electrode material using the plant-derived porous carbon material of Example 1. An electrode prepared using the plant-derived porous carbon material of Example 1 may have an overvoltage for oxygen reduction substantially equal to that of a platinum electrode and produce a large current output. This electrode may sufficiently exhibit an oxygen reduction ability under a pH-neutral condition, which increases the versatility of the electrode. Thus, this electrode may have a high applicability to various types of devices and apparatuses in which an oxygen reduction electrode capable of exhibiting an oxygen reduction ability under a pH-neutral condition is anticipated.

Example 2

In Example 2, a variation of the electrode material of Example 1 is described. In an electrode material of Example 2, a porous carbon material includes an oxygen reduction catalyst supported thereon. Specifically, iron phthalocyanine (FePc) and cobalt(II)tetra(methoxyphenyl)porphyrin (CoTMPP) were used as oxygen reduction catalysts.

In Example 2, 0.1 g of the plant-derived porous carbon material prepared in Example 1, 250 µl of 10% Nafion, 5 ml of 2-propanol, and 0.05 g of iron phthalocyanine (FePc) or cobalt(II)tetra(methoxyphenyl)porphyrin (CoTMPP) were mixed to prepare a paste. Then, a test oxygen reduction electrode was prepared using the paste as in Example 1. The oxygen reduction ability of the test oxygen reduction electrode was evaluated as in Example 1.

Figure 4:
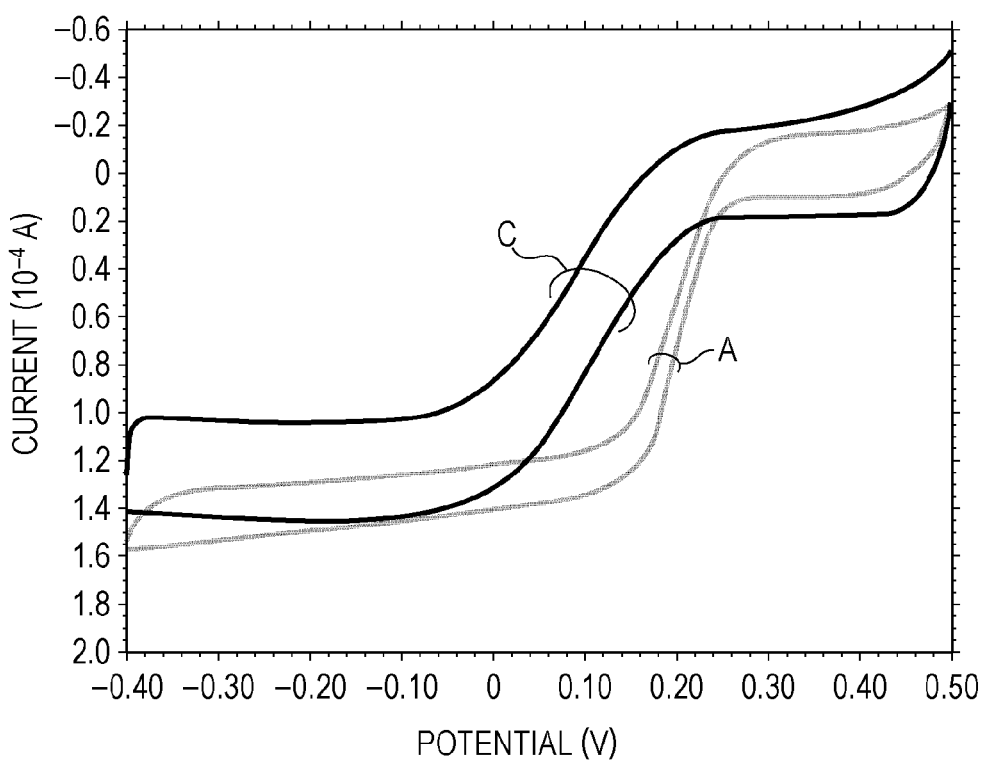
FIG. 4 is a graph showing the results of evaluation of the oxygen reduction ability of a test oxygen reduction electrode prepared in Example 2.
Figure 5:
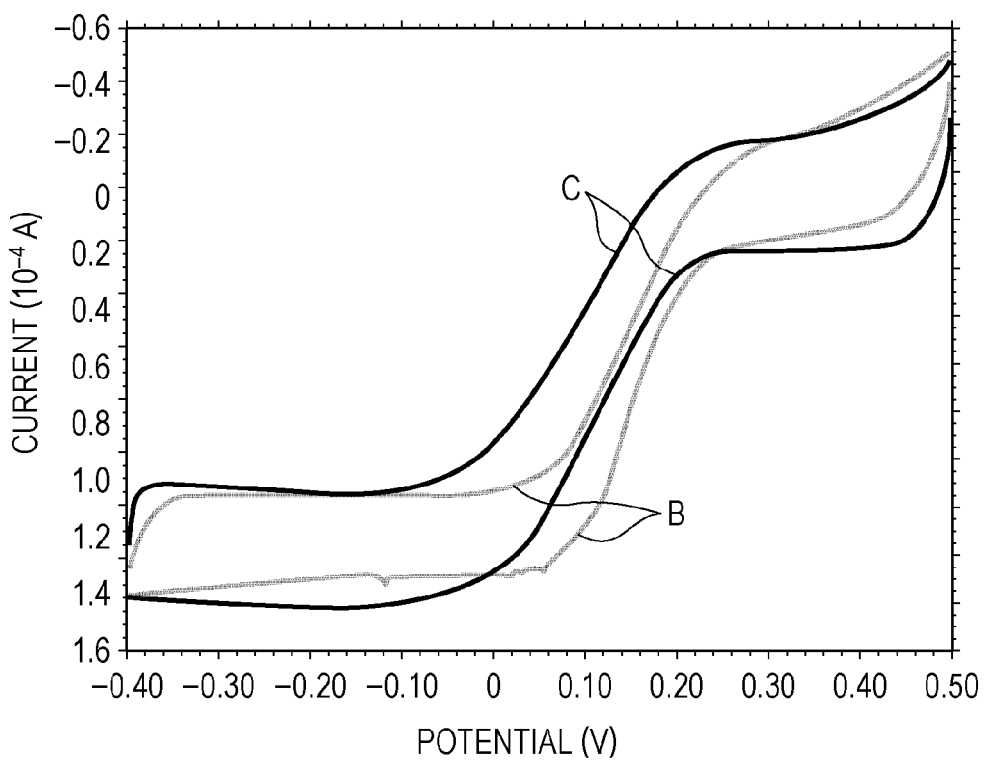
FIG. 5 is a graph showing the results of evaluation of the oxygen reduction ability of the test oxygen reduction electrode of Example 2.

FIG. 4 shows the evaluation results of a test oxygen reduction electrode prepared using iron phthalocyanine (FePc), which are shown by the curves "A". FIG. 5 shows the evaluation results of a test oxygen reduction electrode prepared using cobalt(II)tetra(methoxyphenyl)porphyrin (CoTMPP), which are shown by the curves "B". When the plant-derived porous carbon material prepared in Example 1 was used in combination both with FePc and with CoTMPP, the test oxygen reduction electrode had a higher performance than that prepared in Example 1 in which the plant-derived porous carbon material was used alone (shown by the curves "C" in FIGS. 4 and 5).

Example 3

Example 3 relates to an electrode according to an embodiment of the present disclosure and to a battery (specifically, metal-air battery) according to an embodiment of the present disclosure. An electrode prepared in Example 3 included a plant-derived porous carbon material having an ability to catalyze oxygen reduction. A battery prepared in Example 3 included a positive electrode (cathode) including a plant-derived porous carbon material having an ability to catalyze oxygen reduction. Specifically, the battery of Example 3 was an aluminium-air primary battery that included a negative electrode (anode) including a material containing aluminium and that generated electric power using oxygen in the air as a positive-electrode-active material. As described above, the plant-derived porous carbon material used was the plant-derived porous carbon material prepared in Example 1. The porous carbon material was supported on a supporting member (specifically, in Example 3, sheet-like material composed of carbon fiber). The electrode of Example 3 was used as the positive electrode of the battery.

In the related art, there have been studies on a method for promoting a cathodic reaction using an alkaline solution as an electrolytic solution in order to increase the output of an aluminium-air battery. However, the positive electrode of the aluminium-air battery using an alkaline solution as an electrolytic solution may become degraded because severe corrosion of aluminium occurs under an alkaline condition and because the alkaline electrolytic solution absorbs carbon dioxide in the air and consequently becomes neutralized gradually.

Thus, these issues may be addressed using the electrode (positive electrode) of Example 3 that causes oxygen to be reduced under a pH-neutral condition.

Specifically, the aluminium-air battery of Example 3 included an electrolytic solution having a pH of 3 or more and 10 or less. In order to maintain the electrolytic solution at a pH of 3 or more and 10 or less, the electrolytic solution may contain a buffer substance or the like. Generally, any buffer substance may be used as long as it has a $pK_a$ of 4 or more and 10 or less.

An aluminium-air battery includes a separator interposed between a negative electrode and a positive electrode. The negative electrode, the positive electrode, the separator interposed between the negative electrode and the positive electrode, and the like are immersed in an electrolytic solution. In other words, the separator constitutes an electrolyte layer that is filled with the electrolytic solution and that allows aluminium ions to migrate between the negative electrode and the positive electrode. Examples of the material of the separator include a porous membrane composed of polyethylene oxide, polyacrylic acid, poly(vinyl alcohol), polyethylene, or polypropylene, various nonwoven fabrics, paper, and cellulose. Examples of the material of the nonwoven fabrics include, but are not limited to, various high-molecular-weight organic compounds such as polyolefin, polyester, cellulose, and polyacrylamide.

The material containing aluminium that constitutes the negative electrode may be a material containing aluminium as a main component. Specific examples of such a material include aluminium and various aluminium alloys. The shape of the negative electrode may be appropriately selected if necessary and may be, for example, foil-like, sheet-like, or plate-like. More specifically, the negative electrode used in Example 3 was an aluminium foil. The negative electrode may be arranged to be replaceable if necessary. The aluminium-air battery preferably has a structure that allows insoluble matter produced as a by-product to be removed when the negative electrode is replaced.

The positive electrode and negative electrode are each connected to a current collector. The current collectors are typically composed of a metal mesh. The material of the metal mesh is not particularly limited and any material may be used as long as it is capable of withstanding the operating conditions for the aluminium-air battery. For example, titanium (Ti), nickel (Ni), and stainless steel (e.g., SUS304) may be used. The pore size of the metal mesh and the like are also not particularly limited and may be set appropriately. The current collectors have an electrolytic-solution permeability.

The electrolytic solution preferably has a pH of 3 or more and 10 or less and typically includes a buffer substance having a $pK_a$ of 4 or more and 10 or less. Examples of the buffer substance include citric acid, ammonium chloride, phosphoric acid, tris(hydroxymethyl)aminomethane, a compound having an imidazole ring, dihydrogen phosphate ions ($H_2PO_4^-$), 2-amino-2-hydroxymethyl-1,3-propanediol (abbreviated as "tris"), 2-(N-morpholino)ethanesulfonic acid (MES), cacodylic acid, carbonic acid ($H_2CO_3$), hydrogen citrate ion, N-(2-acetamide)imino diacetate (ADA), piperazine-N,N'-bis(2-ethanesulfonic acid) (PIPES), N-(2-acetamide)-2-aminoethanesulfonic acid (ACES), 3-(N-morpholino)propanesulfonic acid (MOPS), N-2-hydroxyethylpiperazine-N'-2-ethanesulfonic acid (HEPES), N-2-hydroxyethylpiperazine-N'-3-propanesulfonic acid (HEPPS), N-[tris(hydroxymethyl)methyl]glycine (abbreviated as "tricine), glycylglycine, and N,N-bis(2-hydroxyethyl)glycine (abbreviated as "bicine"). Examples of a compound from which dihydrogen phosphate ions ($H_2PO_4^-$) are produced include sodium dihydrogenphosphate ($NaH_2PO_4$) and potassium dihydrogenphosphate ($KH_2PO_4$). Examples of the compound having an imidazole ring include imidazole, triazole, a pyridine derivative, a bipyridine derivative, and an imidazole derivative (e.g., histidine, 1-methylimidazole, 2-methylimidazole, 4-methylimidazole, 2-ethylimidazole, imidazole-2-carboxylic acid ethyl ester, imidazole-2-carboxaldehyde, imidazole-4-carboxylic acid, imidazole-4,5-dicarboxylic acid, imidazole-1-yl-acetic acid, 2-acetylbenzimidazole, 1-acetylimidazole, N-acetylimidazole, 2-aminobenzimidazole, N-(3-aminopropyl)imidazole, 5-amino-2-(trifluoromethyl)benzimidazole, 4-azabenzimidazole, 4-aza-2-mercaptobenzimidazole, benzimidazole, 1-benzylimidazole, or 1-butylimidazole). If necessary, the electrolytic solution may include a neutralizer, which is at least one acid selected from the group consisting of hydrochloric acid (HCl), acetic acid ($CH_3COOH$), phosphoric acid ($H_3PO_4$), sulfuric acid ($H_2SO_4$), and the like. The electrolytic solution may be composed of a substance containing halide ions (e.g., chloride ions, bromide ions, iodide ions, or fluoride ions) or the like. For example, when an electrolytic solution is composed of a substance containing chloride ions, the electrolytic solution is composed of NaCl, KCl, or the like. The electrolytic solution may include ionic liquid. Any ionic liquid known in the related art may be used if necessary.

A gas-liquid separation membrane constituting a container that houses the electrolytic solution may be, but is not limited to, a polytetrafluoroethylene (PTFE) membrane or the like. The shape of the container may be selected appropriately if necessary. Examples of the shape of a battery case (container) that houses a positive electrode, a negative electrode, a separator, an electrolytic solution, and the like include a coin shape, a plate shape, a cylinder shape, and a multilayer-body shape. The battery case may have an open-to-the-air structure that allows the positive electrode and the like to be fully exposed to the air or a confined structure that includes a gas (air)-introduction tube and an exhaustion tube.

When an aluminium-air battery is producing electric power, the reactions shown by Formulae (31) to (33) occur at its negative electrode.

$$Al \rightarrow Al^{3+} + 3e^- \tag{31}$$

$$Al^{3+} + 6H_2O \rightarrow [Al(H_2O)_6]^{3+} \tag{32}$$

$$[Al(H_2O)_6]^{3+} \rightarrow [Al(OH)_6]^{3-} + 6H^+ \tag{33}$$

Equations (32) and (33) lead to the following equation.

$$Al^{3+} + 6H_2O \rightarrow [Al(OH)_6]^{3-} + 6H^+ \tag{34}$$

Thus, $Al^{3+}$ migrates from the negative electrode to the positive electrode through the separator, which generates electric energy. In the positive electrode, $H^+$ transported through the separator filled with the electrolytic solution and electrons transported from the negative electrode cause oxygen in the air to be reduced. Thus, water is produced.

Figure 6:
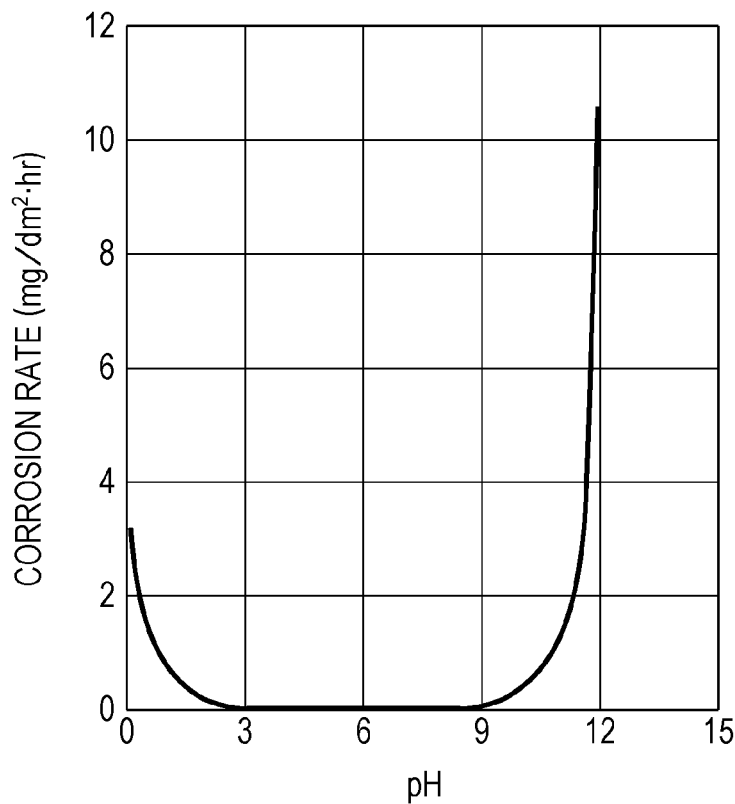
FIG. 6 is a graph showing the relationship between the corrosion rate of aluminium and pH.

As shown in Equation (34), protons accumulate on the surface of the negative electrode. If no measures are taken to avoid the accumulation, the pH of the surface of the negative electrode is reduced and, as a result, self-corrosion of aluminium may occur, which disadvantageously promotes generation of hydrogen gas. When the electrolytic solution contains a buffer substance having $pK_a$ of 4 or more and 10 or less, the action of the buffer substance allows the pH of the surface of the negative electrode to be maintained substantially neutral (e.g., pH of 3 or more and 10 or less). In this case, self-corrosion of aluminium and the resulting promotion of the generation of hydrogen gas do not occur. FIG. 6 shows the relationship between the corrosion rate of aluminium and pH. At a pH of 3 or more and 10 or less, little corrosion occurs or the corrosion rate is extremely small, and therefore the generation of hydrogen gas may be suppressed.

In Example 3, an electrode was prepared by the following method. Specifically, 1.0 g of the plant-derived porous carbon material prepared in Example 1, 0.5 g of a vapor-grown carbon fiber "VGCF-H", 0.25 g of iron phthalocyanine, 0.1 g of poly(vinylidene fluoride) (PVDF), and 8 ml of an N-methyl-2-pyrrolidone (NMP) solvent were mixed and then kneaded to prepare a paste. The vapor-grown carbon fiber "VGCF-H" served as a conduction-assisting agent, iron phthalocyanine served as an oxygen reduction catalyst, and PVDF served as a binder. The paste was applied to a supporting member, and the resulting supporting member was dried to prepare an electrode of Example 3. The vapor-grown carbon fiber "VGCF-H" was used in order to improve electric conductivity and to increase ease of film-formation.

Figure 7:
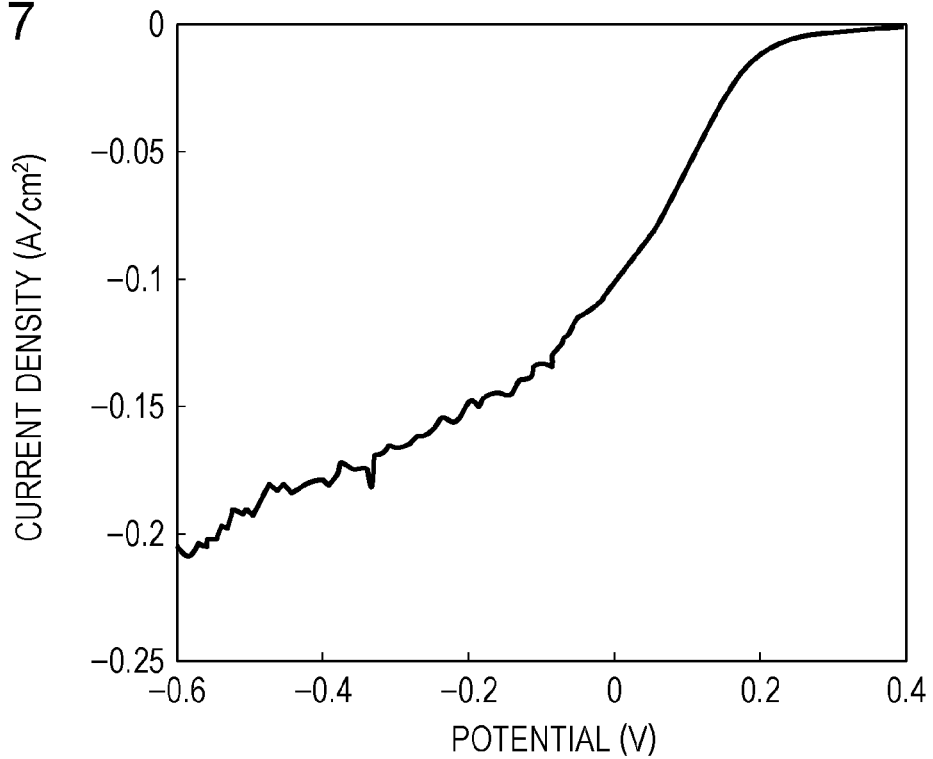
FIG. 7 is a graph showing the results of evaluation of the oxygen reduction ability of an electrode prepared in Example 3.

The oxygen reduction ability of the electrode of Example 3 was evaluated using the same apparatus as in Example 1 by linear sweep voltammetry, which is a method in which a current at an electrode is measured while the potential of the electrode is continuously changed. The electrode of Example 3 was subjected to an electrochemical measurement in an air-saturated aqueous NaCl solution (4 mol/l). FIG. 7 shows the results. It was confirmed that the electrode of Example 3 had a good performance as an electrode. Specifically, the electrode of Example 3 had an electric current density of about 0.2 A/cm$^2$, which was higher than the highest electric current density (40 mA/cm$^2$) that has been reported to date.

Figure 8A:
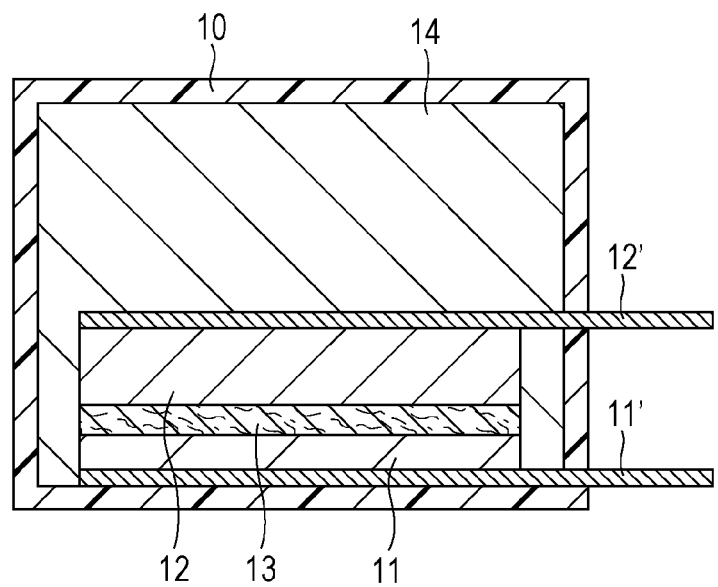
FIGS. 8A and 8B are schematic cross-sectional views of a battery prepared in Example 3.
Figure 9:
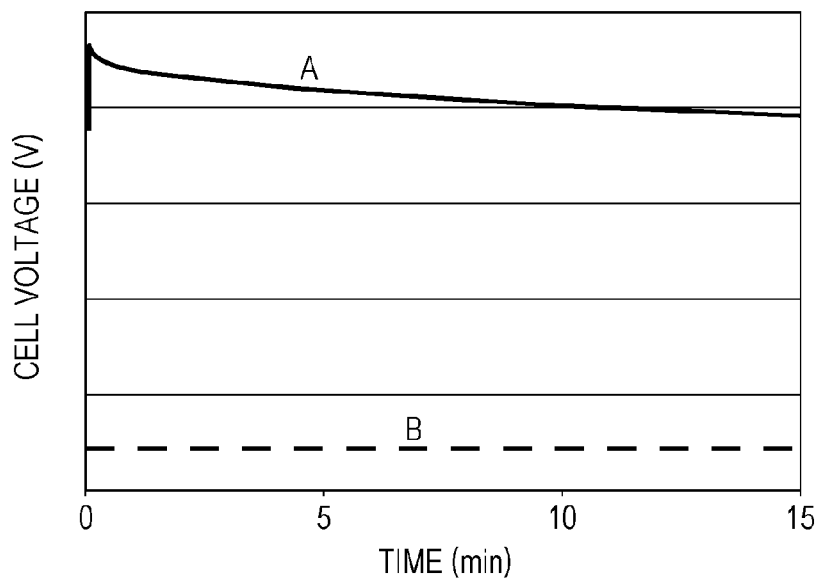
FIG. 9 is a graph showing the cell voltages of the battery of Example 3, which were recorded while the battery was controlled so that a predetermined load was applied to the battery and a certain amount of current flowed.

Then, a metal-air battery including a negative electrode with a negative-electrode-active material including a metal and an alloyed material was prepared. Specifically, an aluminium-air primary battery including a negative electrode (anode) composed of aluminium (see the schematic cross-sectional view thereof shown in FIG. 8A) was prepared and then subjected to an electrochemical evaluation. More specifically, the battery of Example 3 included a positive electrode (cathode) 11 that was the electrode according to an embodiment of the present disclosure, a negative electrode (anode) 12 composed of aluminium, a separator 13 composed of nonwoven fabric, which was interposed between the positive electrode 11 and the negative electrode 12, an electrolytic solution 14, a battery case 10 that housed the above-described components, and current collectors 11' and 12' composed of a titanium mesh, which were attached to the positive electrode 11 and the negative electrode 12, respectively. The electrolytic solution 14 was an aqueous sodium chloride solution (3 mol/l). The battery case 10 composed of a PTFE film also served as a container constituted by a gas-liquid separation membrane. The negative electrode 12 was a square aluminium foil having a size of 10 mm×10 mm×0.17 mm (thickness). The positive electrode 11 was the electrode of Example 3 having a size of 10 mm×10 mm×0.2 mm (thickness). The cell voltage of the battery was recorded while the battery was controlled so that a predetermined load was applied to the battery and a certain amount of current (2 mA) flowed. FIG. 9 shows the results.

For comparison, 1.0 g of vapor-grown carbon fiber "VGCF-H", which was the material used in Comparative Example 1A, 0.1 g of poly(vinylidene fluoride) (PVDF), and 8 ml of N-methyl-2-pyrrolidone (NMP) were mixed and then kneaded to prepare a paste. The paste was applied to a supporting member, and then the resulting supporting member was dried to prepare an electrode of Comparative Example 3. Subsequently, an aluminium-air battery was prepared using this electrode and then subjected to an electrochemical evaluation as in Example 3. FIG. 9 shows both the results of electrochemical evaluations in Example 3 and Comparative Example 3. In FIG. 9, the line denoted by "A" shows the data of Example 3 and the line denoted by "B" shows the data of Comparative Example 3.

FIG. 9 shows that the aluminium-air battery of Comparative Example 3 had little performance as a battery and, on the other hand, the aluminium-air battery of Example 3 had a good performance. The output characteristics of the aluminium-air battery of Example 3 were determined at a battery voltage of 0.95 V. As a result, it was confirmed that the aluminium-air battery of Example 3 continued producing electric power for 3 hours or more since it started generating electric power (started electric discharge). The maximum electric current density measured at a battery voltage of 0.7 V was about 0.070 A/cm$^2$ and the output power was about 50 mW/cm$^2$.

Figure 8B:
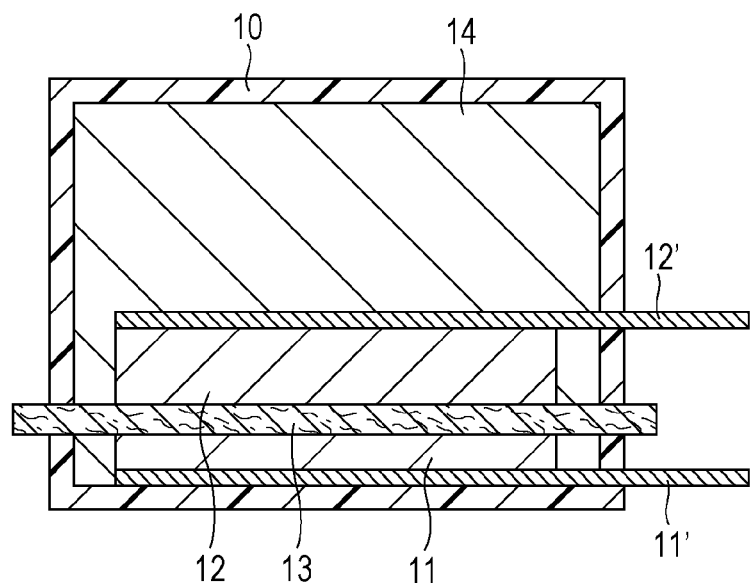

As shown by the schematic cross-sectional view in FIG. 8B, an edge of the separator 13 may protrude from the battery case 10. In this case, a space containing the positive electrode and a space containing the negative electrode can be completely separated. This avoids the reaction product (aluminium hydroxide) produced at the negative electrode from moving to the positive-electrode side, which elongates the service life of the battery.

Figure 10:
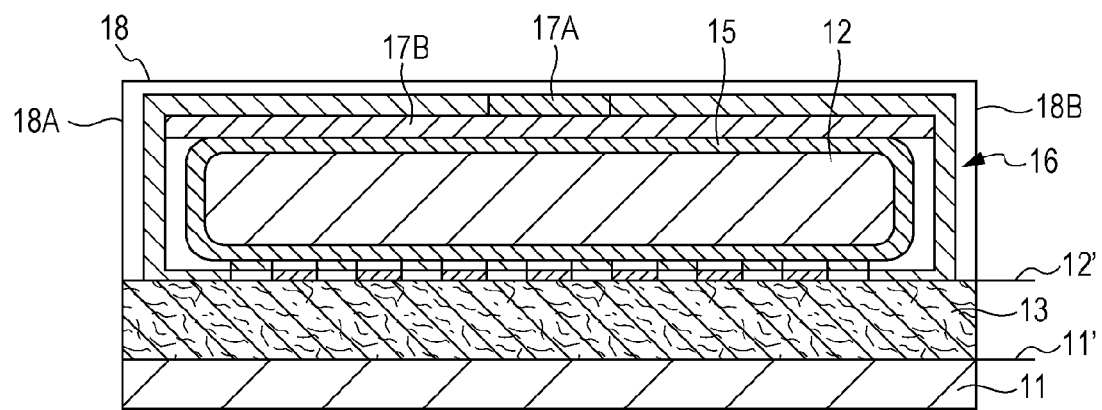
FIG. 10 is a schematic cross-sectional view of a variation of the battery of Example 3.

The negative electrode 12 of the aluminium-air battery may be arranged to be replaceable. As shown in FIG. 10, the negative electrode 12 is housed in a sack-shaped membrane 15, the negative electrode 12 housed in the membrane 15 is housed in a cartridge 16, and the cartridge 16 is housed in a cartridge-housing portion 18. The sack-shaped membrane 15 allows the electrolytic solution 14 to pass therethrough. The cartridge-housing portion 18 is disposed on the separator 13. The reference numerals 17A and 17B denote extrusion units. The cartridge-housing portion 18 includes a cartridge-insertion port 18A through which the cartridge 16 is inserted from the outside to the inside and a cartridge-ejection port 18B through which the cartridge 16 is ejected outward.

Figure 11A:
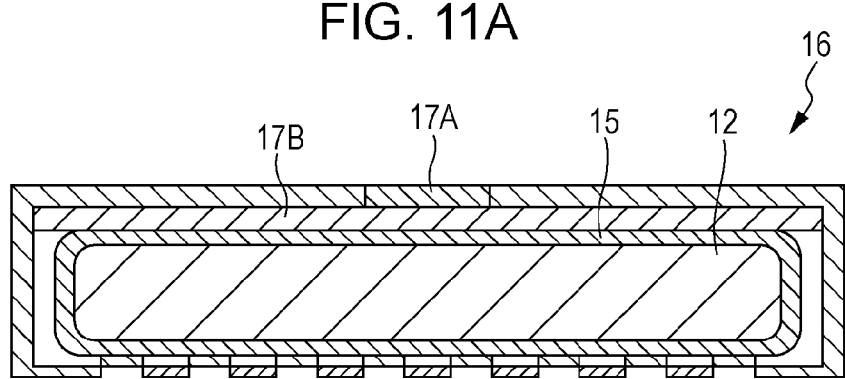
FIG. 11A is a cross-sectional view of a cartridge of the battery of Example 3 shown in FIG. 10, which has not yet been used.
Figure 11B:
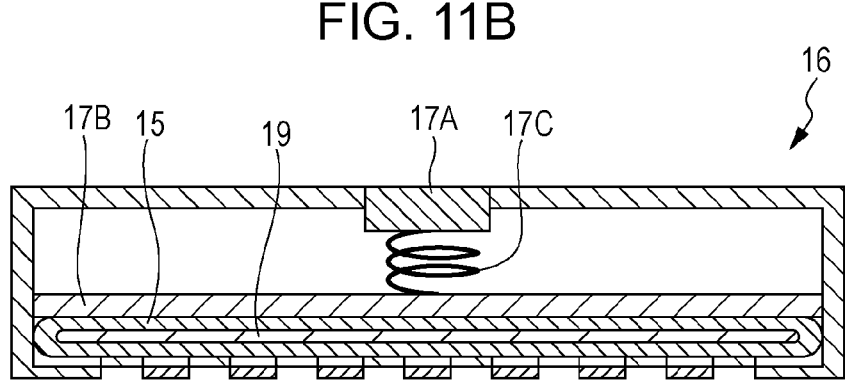
FIG. 11B is a cross-sectional view of a cartridge of the battery of Example 3 shown in FIG. 10, which has been used.
Figure 11C:
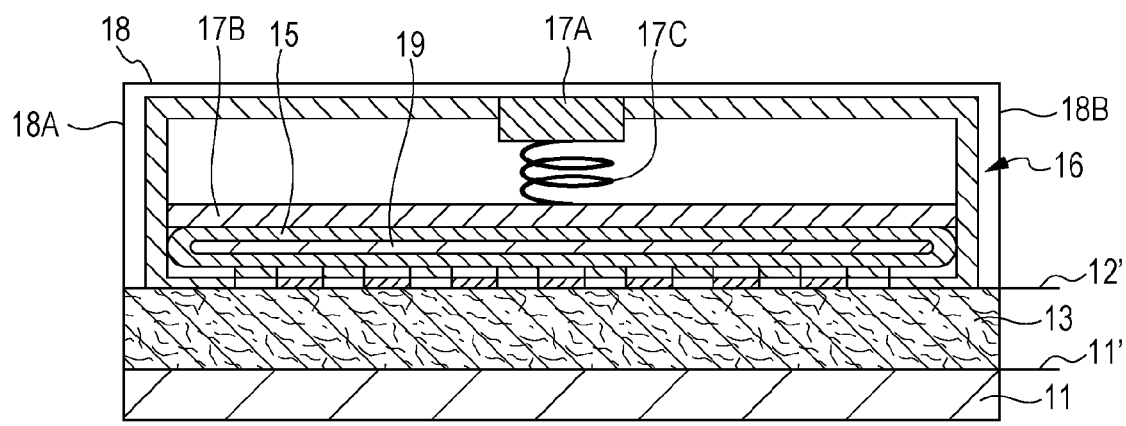
FIG. 11C is a schematic cross-sectional view of the battery of Example 3, which has been used.
Figure 12:
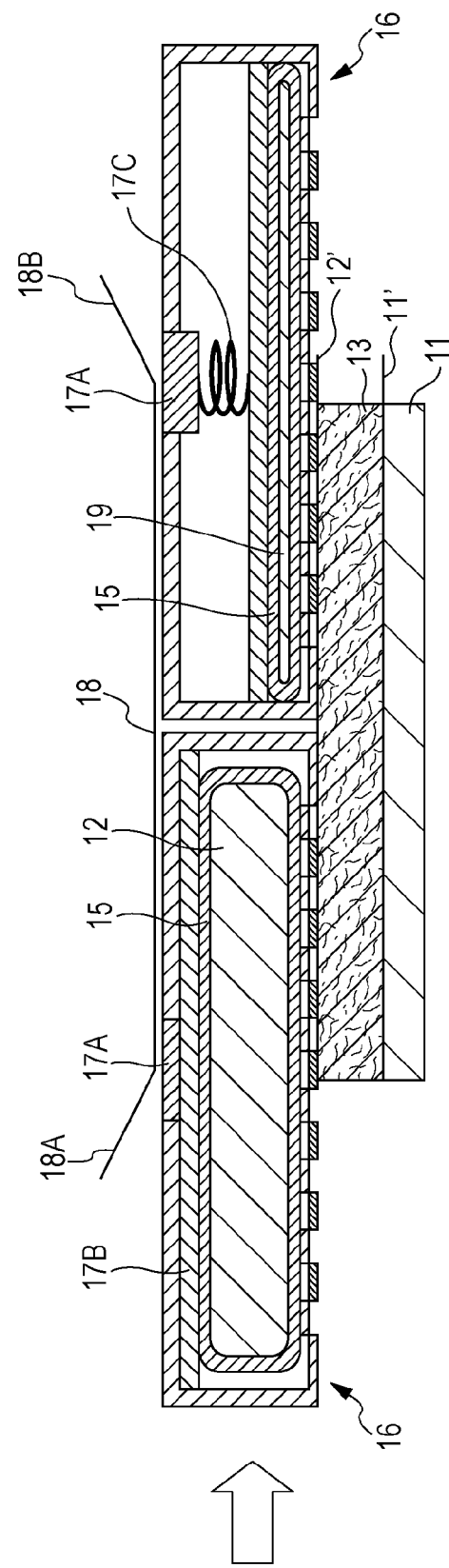
FIG. 12 is a schematic cross-sectional view of the battery of Example 3 for explaining a method for replacing the cartridge of the battery of Example 3.

FIG. 11A shows the cartridge 16 that has not yet been used. FIG. 11B shows the cartridge 16 in which the negative electrode 12 serving as a "fuel" is depleted. FIG. 11C shows the aluminium-air battery in which the negative electrode 12 in the cartridge 16 is depleted. After the negative electrode 12 is depleted, the sack-shaped membrane 15 contains a by-product that is aluminium hydroxide 19 confined therein. In FIGS. 11B, 11C, and 12, the reference numeral 17C denotes a spring for extrusion which is fixed to the extrusion units 17A and 17B at the respective ends of the spring. In FIG. 11A, the spring 17C is omitted. The extrusion unit 17A is fixed to the cartridge 16. The extrusion unit 17B, which is pressed by the spring 17C, presses the negative electrode 12 against the separator 13.

A used cartridge 16 may be replaced with an unused cartridge 16 as described below. As shown in FIG. 12, the cartridge-insertion port 18A is opened, and the unused cartridge 16 is inserted into the cartridge-housing portion 18 through the cartridge-insertion port 18A. The used cartridge 16 is extruded outward through the cartridge-ejection port 18B. When the used cartridge 16 is completely extruded through the cartridge-ejection port 18B, the unused cartridge 16 is set at a predetermined position as shown in FIG. 10. In this unused cartridge 16, the extrusion unit 17B presses the negative electrode 12 against the separator 13.

Alternatively, the negative electrode may be composed of an aluminium alloy such as Al—Li, Al—Mg, Al—Sn, or Al—Zn. In another case, zinc, a zinc alloy, magnesium, and a magnesium alloy may also be used. An aluminium-air battery having a good performance comparable to that of the aluminium-air battery of Example 3 was prepared using an electrolytic solution prepared by adding, as a buffer substance, 1.0 mol of imidazole per liter of the electrolytic solution. An aluminium-air battery having a good performance comparable to that of the aluminium-air battery of Example 3 was prepared using an electrolytic solution prepared by adding, as a buffer substance, 1.0 mol of citric acid per liter of the electrolytic solution.

Example 4

In Example 4, variations of the electrode and the battery of Example 3 are described. A battery prepared in Example 4 also included a positive electrode (cathode) including the plant-derived porous carbon material having an ability to catalyze oxygen reaction. The positive electrode included the same components and had the same structure as the electrode described in Example 3. The battery of Example 4 was an enzymatic biofuel cell shown by the schematic cross-sectional view thereof in FIG. 13.

Figure 13:
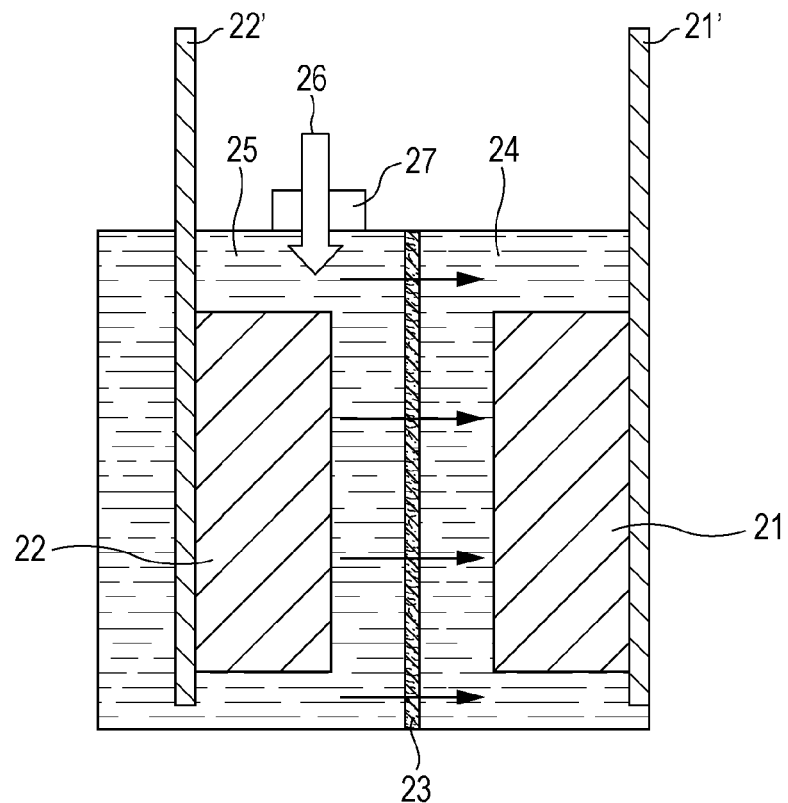
FIG. 13 is a schematic cross-sectional view of a battery prepared in Example 4.

The enzymatic biofuel cell of Example 4 was an immersion-type fuel cell including a positive electrode (air electrode, cathode) 21 that was the electrode according to an embodiment of the present disclosure and a negative electrode (fuel electrode, anode) 22, which were both being in contact with an electrolyte. An oxygen-reduction enzyme was present on the surface of the negative electrode 22. The expression "the surface of an electrode" herein collectively refers to the outer surface of the electrode and the inner surfaces of pores that are present inside the electrode. Current collectors 21' and 22' were arranged to be in contact with the positive electrode 21 and the negative electrode 22, respectively. The current collectors 21' and 22' had, for example, a mesh-like shape and thus allowed an electrolytic solution and air to pass therethrough. As shown in FIG. 13, for example, the inner surface of the positive electrode 21 was arranged to be in contact with a liquid phase (solution) and the outer surface of the positive electrode 21 was arranged to be in contact with a gas phase (air) via the current collector 21' interposed between the positive electrode 21 and the gas phase (air). The inner surface of the negative electrode 22 was arranged to be in contact with a liquid phase (solution) and the outer surface of the negative electrode 22 was arranged to be in contact with a liquid phase (solution) via the current collector 22' interposed between the negative electrode 22 and the liquid phase. A cathode-solution section 24 and an anode-solution section 25 were provided in the peripheries of the positive electrode 21 and the negative electrode 22, respectively. A separator 23 composed of unwoven fabric was interposed between the cathode-solution section 24 and the anode-solution section 25. The battery further included a fuel-solution-introduction port 27 through which a fuel solution 26 was introduced. The fuel-solution-introduction port 27 was communicated with the anode-solution section 25.

The negative electrode 22 was a fuel electrode, which was prepared by fixing an oxidoreductase on the surface of an electrode composed of a conductive porous material or the like. Any material known in the related art may be used as the conductive porous material constituting the negative electrode 22. In particular, carbon-based materials such as porous carbon, carbon pellets, carbon felt, carbon paper, carbon fiber, and layered carbon particles may be preferably used. The porous carbon may be the plant-derived porous carbon material according to an embodiment of the present disclosure. When the fuel component is glucose, the enzyme fixed to the surface of the negative electrode 22 may be glucose dehydrogenase (GDH) that allows glucose to be decomposed. When the fuel component is a monosaccharide such as glucose, the negative electrode preferably further includes a coenzyme oxidase or an electron-transfer mediator fixed to the surface thereof together with an oxidase such as GDH which promotes oxidation of a monosaccharide and which allows the monosaccharide to be decomposed. The coenzyme oxidase oxidizes a coenzyme reduced by an oxidase (e.g., $NAD^+$ or $NADP^+$) and a reduced form of a coenzyme (e.g., NADH or NADPH). An example of a coenzyme oxidase is diaphorase. When a coenzyme is again converted into its oxidized form, electrons are produced due to the action of the coenzyme oxidase. The electrons are transferred from the coenzyme oxidase to the negative electrode 22 via the electron-transfer mediator.

A compound including a quinone skeleton is preferably used as the electron-transfer mediator. More preferably, a compound including a naphthoquinone skeleton is used. Specifically, 2-amino-1,4-naphthoquinone (ANQ), 2-amino-3-methyl-1,4-naphthoquinone (AMNQ), 2-methyl-1,4-naphthoquinone (VK3), 2-amino-3-carboxy-1,4-naphthoquinone (ACNQ), and the like may be used. Examples of the compound including a quinone skeleton include the compound including a naphthoquinone skeleton, anthraquinone, and its derivatives. If necessary, one or more other compounds that serve as the electron-transfer mediator may be fixed on the surface of the negative electrode 22 together with the compound including a quinone skeleton.

When the fuel component is a polysaccharide, a degrading enzyme that promotes decomposition (e.g., hydrolysis) of the polysaccharide to produce a monosaccharide such as glucose is desirably fixed on the surface of the negative electrode 22 together with the above-described oxidase, coenzyme oxidase, coenzyme, and electron-transfer mediator. Herein, the term "polysaccharide" is used in the broad sense of the term and refers to any carbohydrate that yields two or more molecules of monosaccharides by hydrolysis. Examples of the "polysaccharide" include oligosaccharides such as a disaccharide, a trisaccharide, and a tetrasaccharide. Specific examples thereof include starch, amylose, amylopectin, glycogen, cellulose, maltose, sucrose, and lactose. These polysaccharides are composed of two or more monosaccharides linked to one another. Each of these polysaccharides includes glucose as a monosaccharide as a linking unit.

Starch contains amylose and amylopectin. Thus, starch is a mixture of amylose and amylopectin. For example, when glucoamylase is used as a polysaccharide-degrading enzyme and glucosedehydrogenase is used as a monosaccharide-degrading oxidase, the fuel component may be a polysaccharide that can be decomposed into glucose by glucoamylase. Examples of such a polysaccharide include starch, amylose, amylopectin, glycogen, and maltose. Glucoamylase is a degrading enzyme that causes hydrolysis of an α-glucan such as starch to produce glucose. Glucosedehydrogenase is an oxidase that causes β-D-glucose to be oxidized into D-glucono-δ-lacton.

The negative electrode 22 is not limited to an electrode including an oxidoreductase fixed on the surface thereof. As long as an oxidoreductase is present on the electrode surface, for example, an electrode including an oxidoreductase and microorganisms, which serve as reaction catalysts, attached on the electrode may also be used.

The fuel solution 26 is a solution containing a fuel component such as a sugar, an alcohol, an aldehyde, a lipid, or a protein or is a solution containing at least one of these fuel components. Specific examples of the fuel component include sugars such as glucose, fructose, and sorbose; alcohols such as methanol, ethanol, propanol, glycerin, and poly(vinyl alcohol); aldehydes such as formaldehyde and acetaldehyde; and organic acids such as acetic acid, formic acid, and pyruvic acid. Fats, proteins, and the above-described organic acids that are intermediate products of sugar metabolism, and the like may also be used as the fuel component. The fuel solution 26 may further include an electrolyte that serves as a proton conductor.

Figure 14:
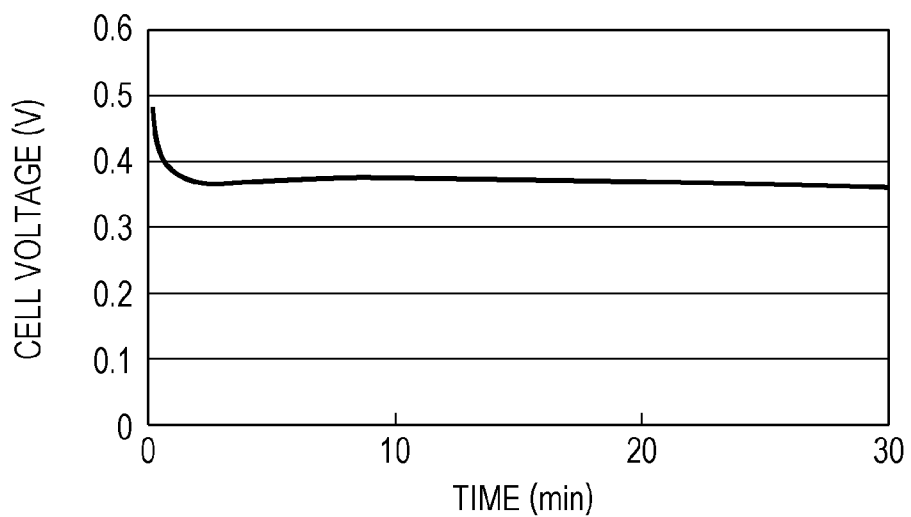
FIG. 14 is a graph showing a cell voltage of the battery of Example 4, which was recorded while the battery was controlled so that a predetermined load was applied to the battery and a certain amount of current flowed.

More specifically, in Example 4, the fuel solution 26 was a phosphate buffer (1 mol/l) containing 0.8 mol/l of glucose. Then, glucosedehydrogenase (GDH) was fixed to the surface of the negative electrode 22 including a conductive porous material. The cell voltage of the battery of Example 4 was recorded as in Example 3. That is, the cell voltage of the battery of Example 4 was recorded while the battery was controlled so that a predetermined load was applied to the battery and a certain amount of current flowed. FIG. 14 shows the results. It was confirmed that the enzymatic biofuel cell of Example 4 had a good performance.

Figure 15:
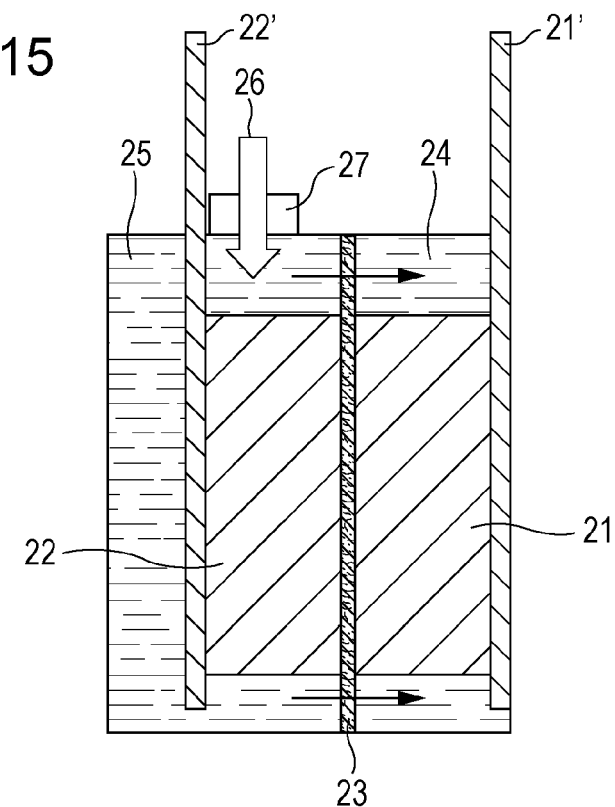
FIG. 15 is a schematic cross-sectional view of a variation of the battery of Example 4.

The battery of Example 4 may be applied to a battery having a "single-cell" structure in which the battery includes a single cell or to a battery in which a plurality of cells are connected to one another in series or in parallel. When a battery includes a plurality of cells, the cells may share a single fuel-solution-introduction port. As shown in FIG. 15, the positive electrode 21 and the negative electrode 22 may be arranged to be in contact with the separator 23. In this case, the separator is impregnated with the solution, and thus the inner surfaces of the positive electrode 21 and the negative electrode 22 are arranged to be in contact with the solution.

A permselective membrane may be used instead of the separator composed of nonwoven fabric. The permselective membrane has a water permeability and is capable of suppressing the permeation of the fuel component and the like contained in the fuel solution 26. The fuel solution 26 introduced into the anode-solution section 25 is then introduced into the cathode-solution section 24 through the permselective membrane. The permselective membrane may also suppress permeation of components other than the fuel component contained in the fuel solution 26. In particular, the permselective membrane preferably suppress permeation of an enzyme or a mediator eluted into the fuel solution 26. This suppresses transfer of the enzyme and the mediator that are present at each electrode to another electrode side, which results in suppression of degradation of battery characteristics. The permselective membrane may suppress permeation of a substance that has an inhibitory effect on the positive electrode 21. For example, when the fuel solution 26 is a commercially-available beverage, the permselective membrane may also suppress permeation of a calorie-free sweetener and permeation of sugars (e.g., fructose) that are difficult to be oxidized by the enzyme of the negative electrode 22. This suppresses degradation of battery characteristics and thus increases power-generation efficiency.

Examples of the permselective membrane include a cellulose membrane and a synthetic polymer membrane. Specific examples of the cellulose membrane include regenerated cellulose membranes (RC) such as cuprammonium rayon (CR) and saponified cellulose acetate (SCA); surface-modified regenerated cellulose membranes such as a hemophan membrane and a vitamin E-coated membrane; and cellulose acetate (CA) membranes such as cellulose diacetate (CDA) and cellulose triacetate (CTA). Examples of the synthetic polymer membrane include polyacrylonitrile (PAN), poly(methyl methacrylate) (PMMA), ethylene-vinylalcohol copolymer (EVA), a polysulfone (PS), a polyamide (PA), and a polyester-polymer alloy.

The average pore size of the permselective membrane may be, for example, 0.5 μm or less in order to efficiently suppress permeation of the fuel component. The average pore size of the permselective membrane is preferably 100 nm or less, more preferably 20 nm or less, and further preferably 10 nm or less in order to enhance the effect of suppressing permeation of the fuel component and to also suppress permeation of components other than the fuel component, such as an enzyme and a mediator. Desirably, the permselective membrane is provided so that the ionic conductivity between the negative electrode 22 and the positive electrode 21 is set to 0.1 S/cm or more, that is, so that the internal resistance of the battery is set to 10Ω or less. This reduces the loss of power generated. The ionic conductivity between the negative electrode 22 and the positive electrode 21 can be determined by an impedance measurement while an electrolytic solution is present therebetween. The permselective membrane desirably has chemical stability in a solution having a pH of 3 to 10 and heat resistance so as not to cause degradation or the like at −20° C. to 120° C. This suppresses degradation or fracture of the permselective membrane in the solution, which allows power generation without problems such as a short-circuit.

In the above-described enzymatic biofuel cell, the fuel solution 26 is introduced into the anode-solution section 25 through the fuel-solution-introduction port 27. The fuel solution is also supplied to the cathode-solution section 24 through the permselective membrane. In this case, since the permselective membrane suppresses permeation of the fuel component contained in the fuel solution 26, a fuel solution having a low concentration of the fuel component is introduced into the cathode-solution section 24. In other words, the fuel solution being in contact with the negative electrode 22 has a higher concentration of the fuel component than a fuel solution being in contact with the positive electrode 21. At the negative electrode 22, the fuel is decomposed by the enzyme fixed to the surface of the negative electrode 22. Thus, electrons are extracted and protons ($H^+$) are generated. At the positive electrode 21, water is produced from the protons transported from the negative electrode 22 through the proton conductor, the electrons transported from the negative electrode 22 through an external circuit, and oxygen contained, for example, in the solution (liquid phase) stored in the cathode-solution section 24 or in the air (gas phase). Since the above-described enzymatic biofuel cell includes the permselective membrane interposed between the anode-solution section 25 and the cathode-solution section 24, which suppresses permeation of the fuel component, diffusion of the fuel component to the positive-electrode-21 side may be suppressed. Therefore, even when the concentration of the fuel component in the fuel solution 26 introduced into the anode-solution section 25 is increased, the concentration of the fuel component contained in the solution introduced into the cathode-solution section 24 may be kept low, which results in suppression of deterioration of the properties of the positive electrode 21. Furthermore, the concentration of the fuel component contained in the solution being in contact with the negative electrode 22 may be kept high, which increases the efficiency of power generation. As a result, an enzymatic biofuel cell that has a battery output greater than or equal to those of the enzymatic biofuel cells known in the related art and that has a larger battery capacity than the enzymatic biofuel cells known in the related art may be realized.

Figure 16:
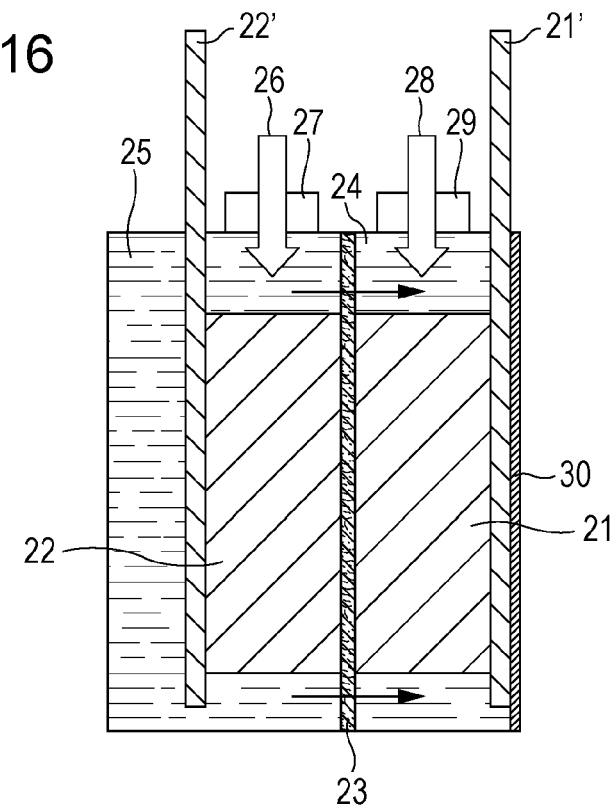
FIG. 16 is a schematic cross-sectional view of another variation of the battery of Example 4.

Alternatively, as shown in FIG. 16, the immersion-type fuel cell may have a structure in which a positive electrode 21 is in contact with a solution 28 containing an electrolyte and the like and a negative electrode 22 is in contact with a fuel solution 26. Optionally, a gas-liquid separation membrane 30 may be arranged to be in contact with the outer surface of the positive electrode 21 so that the positive electrode 21 is brought into contact with a gas phase (air) with the gas-liquid separation membrane 30. In another case, the positive electrode 21 may be arranged to be in direct contact with the gas phase (air) by making the surface of the positive electrode 21 water repellent. Current collectors 21' and 22' are attached to the positive electrode 21 and the negative electrode 22, respectively. An anode-solution section 25 and a cathode-solution section 24 are provided in the peripheries of the negative electrode 22 and the positive electrode 21, respectively. A permselective membrane 23' is interposed between the positive electrode 21 and the negative electrode 22. A fuel-solution-introduction port 27 communicated with the anode-solution section 25 and a solution-introduction port 29 communicated with the cathode-solution section 24 are separately disposed. The fuel solution 26 is introduced into the anode-solution section 25 through the fuel-solution-introduction port 27. The solution 28 containing an electrolyte, which is a solution different from the fuel solution 26, is introduced into the cathode-solution section 24 through the solution-introduction port 29.

Examples of the solution 28 introduced into the cathode-solution section 24 include, but are not limited to, an aqueous solution (electrolytic solution) containing an electrolyte such as dihydrogen phosphate or an imidazole compound; an aqueous potassium chloride solution; and ionic liquid. The solution 28 serves mainly as a proton conductor.

In this enzymatic biofuel cell, the fuel solution 26 is introduced into the anode-solution section 25 through the fuel-solution-introduction port 27, and the solution 28 such as an electrolytic solution is introduced into the cathode-solution section 24 through the solution-introduction port 29. The fuel component contained in the fuel solution 26 stored in the anode-solution section 25 transfers into the solution 28 contained in the cathode-solution section 24. Since the permselective membrane 23' suppresses permeation of the fuel component, the concentration of the fuel component in the periphery of the positive electrode 21 is kept lower than in the periphery of the negative electrode 22. The osmotic pressure of the solution 28 is desirably set higher than that of the fuel solution 26 by, for example, setting the ion concentration of the solution 28 introduced into the cathode-solution section 24 to be higher than that of the fuel solution 26. This further reduces the amount of fuel component transferred from the fuel solution 26 by permeating the permselective membrane 23'. In this enzymatic biofuel cell, at the negative electrode 22, the fuel is decomposed by an enzyme fixed to the surface of the negative electrode 22. Thus, electrons are extracted and protons ($H^+$) are generated. At the positive electrode 21, water is produced from the protons transported from the negative electrode 22 through the proton conductor, the electrons transported from the negative electrode 22 through an external circuit, and oxygen contained, for example, in the solution 28 stored in the cathode-solution section 24 or in the gas phase (air) being in contact with the current collector 21' via the gas-liquid separation membrane 30 interposed between the gas phase and the current collector 21'.

In this enzymatic biofuel cell, the solution-introduction port 29 is communicated with the cathode-solution section 24 and disposed separately from the fuel-solution-introduction port 27. Therefore, different solutions can be introduced into the anode-solution section 25 and the cathode-solution section 24. In addition, the permselective membrane 23' is interposed between the anode-solution section 25 and the cathode-solution section 24. Therefore, even when the concentration of the fuel component contained in the fuel solution 26 introduced into the anode-solution section 25 is increased, the amount of the fuel component transferred into the solution 28 introduced into the cathode-solution section 24 may be kept low. As a result, the concentration of the fuel component in the periphery of the positive electrode 21 may be kept low, which results in suppression of deterioration of the properties of the positive electrode 21.

The preferred embodiments of the present disclosure are described above with reference to examples. The present disclosure is not limited to these embodiments, and various modifications may be made. Although chaff is used as the raw material of the porous carbon material in above-described examples, another plant may be used as the raw material. Examples of the other plant include straw, reeds, or wakame stems, vascular plants living on land, pteridophytes, bryophytes, algae, and seaweeds. These materials may be used alone or in a mixture of two or more. Specifically, for example, rice straw (e.g., straw of rice "Isehikari" produced in Kagoshima prefecture, Japan) may be used as a plant-derived material, that is, the raw material of the porous carbon material. In this case, the straw (raw material) is carbonized to be converted into a carbonaceous substance (precursor of a porous carbon material), and the carbonaceous substance is then treated with an acid to produce a porous carbon material. In another case, reeds, which are poaceous plants, may be used as a plant-derived material, that is, the raw material of the porous carbon material. In this case, the reeds (raw material) are carbonized to be converted into a carbonaceous substance (precursor of a porous carbon material), and the carbonaceous substance is then treated with an acid to produce a porous carbon material. A porous carbon material produced by being treated using an alkali such as an aqueous sodium hydroxide solution instead of an aqueous hydrofluoric acid solution has the similar properties to that of a porous carbon material produced by being treated with an acid.

Alternatively, wakame stems (produced in Sanriku, Iwate prefecture, Japan) may be used as the plant-derived material, that is, the raw material of the porous carbon material. In this case, the wakame stems (raw material) are carbonized to be converted into a carbonaceous substance (precursor of a porous carbon material), and the carbonaceous substance is then treated with an acid to produce a porous carbon material. Specifically, for example, the wakame stems are carbonized by being heated at about 500° C. The wakame stems (raw material) may be treated with an alcohol or the like prior to being heated. A specific example of a method for treating wakame stems is a method in which wakame stems are immersed in ethyl alcohol or the like. This reduces the moisture content of the raw material and causes elements other than carbon and the mineral component that are contained in the final product (i.e., porous carbon material) to be eluted. Through the treatment with an alcohol, the evolution of gas during the carbonization may be suppressed. More specifically, the wakame stems are immersed in ethyl alcohol for 48 hours. An ultrasonic treatment is preferably performed in ethyl alcohol. The resulting wakame stems are heated at 500° C. for 5 hours in a nitrogen gas stream to be carbonized. Thus, a carbide is produced. Through the above-described preliminary carbonization treatment, the amount of tar component that is to be produced in the next carbonization process may be reduced or may be removed. Subsequently, 10 g of the carbide is placed in a crucible composed of alumina, heated to 1,000° C. at a rate of temperature rise of 5° C./min in a nitrogen gas stream (10 l/min), and then carbonized at 1,000° C. for 5 hours to be converted into a carbonaceous substance (precursor of a porous carbon material). Then, the temperature is decreased to a room temperature. The nitrogen gas is kept flowing during the carbonization and cooling. The precursor of the porous carbon material is treated with an acid by being immersed in an aqueous hydrofluoric acid solution (46% by volume) overnight. The resulting material is then washed with water and ethyl alcohol until the pH of the material reaches 7 and then dried. Thus, a porous carbon material is produced.

According to an embodiment of the present disclosure, the following electrodes, electrode materials, and batteries may be provided.

[1]<electrode> An electrode including a plant-derived porous carbon material having an ability to catalyze oxygen reduction.

[2] An electrode based on the electrode described in [1], wherein the porous carbon material is used for oxygen reduction at a pH of 3 or more and 10 or less.

[3] An electrode based on the electrode described in [1] or [2], wherein the specific surface area of the porous carbon material is 100 m$^2$/g or more as measured by the nitrogen BET method and the pore volume of the porous carbon material is 0.2 cm$^3$/g or more as measured by the BJH method and 0.1 cm$^3$/g or more as measured by the MP method.

[4] An electrode based on the electrode described in any one of [1] to [3], wherein the oxygen reduction starting potential of the porous carbon material is more noble than 0.15 V as measured versus a Ag/AgCl reference electrode.

[5] An electrode based on the electrode described in any one of [1] to [4], wherein the porous carbon material includes an oxygen reduction catalyst supported thereon.

[6] An electrode based on the electrode described in [5], wherein the oxygen reduction catalyst is at least one material selected from the group consisting of a noble metal, a transition-metal oxide, a transition-metal porphyrin, phthalocyanine, a porphyrin polymer, a phthalocyanine polymer, perovskite, and a product of pyrolysis of a cobalt salt using polyacrylonitrile.

[7] An electrode based on the electrode described in any one of [1] to [6], wherein the porous carbon material is supported on a supporting member.

[8] An electrode based on the electrode described in any one of [1] to [7], wherein the electrode is used as a positive electrode of a battery.

[9]<electrode material> An electrode material including a plant-derived porous carbon material having an ability to catalyze oxygen reduction.

[10] An electrode material based on the electrode material described in [9], wherein the porous carbon material is used for oxygen reduction at a pH of 3 or more and 10 or less.

[11] An electrode material based on the electrode material described in [9] or [10], wherein the specific surface area of the porous carbon material is 100 m$^2$/g or more as measured by the nitrogen BET method and the pore volume of the porous carbon material is 0.2 cm$^3$/g or more as measured by the BJH method and 0.1 cm$^3$/g or more as measured by the MP method.

[12] An electrode material based on the electrode material described in any one of [9] to [11], wherein the oxygen reduction starting potential of the porous carbon material is more noble than 0.15 V as measured versus a Ag/AgCl reference electrode.

[13]<battery> A battery including a positive electrode including a plant-derived porous carbon material having an ability to catalyze oxygen reduction.

[14] A battery based on the battery described in [13], wherein the porous carbon material is used for oxygen reduction at a pH of 3 or more and 10 or less.

[15] A battery based on the battery described in [13] or [14], wherein the specific surface area of the porous carbon material is 100 m$^2$/g or more as measured by the nitrogen BET method and the pore volume of the porous carbon material is 0.2 cm$^3$/g or more as measured by the BJH method and 0.1 cm$^3$/g or more as measured by the MP method.

[16] A battery based on the battery described in any one of [13] to [15], wherein the oxygen reduction starting potential of the positive electrode is more noble than 0.15 V as measured versus a Ag/AgCl reference electrode.

[17] A battery based on the battery described in any one of [13] to [16], wherein the battery includes an electrolytic solution containing a buffer substance.

[18] A battery based on the battery described in [17], wherein the buffer substance has a pK$_a$ of 4 or more and 10 or less.

It should be understood by those skilled in the art that various modifications, combinations, sub-combinations and alterations may occur depending on design requirements and other factors insofar as they are within the scope of the appended claims or the equivalents thereof.

What is claimed is:

1. An electrode comprising a plant-derived porous carbon material that catalyzes oxygen reduction at the electrode.

2. The electrode according to claim 1,
   wherein the plant-derived porous carbon material is a carbonized material treated with at least one of an acid and an alkali.

3. The electrode according to claim 1, wherein:
   the porous carbon material is used for oxygen reduction at a pH of 3 or more and 10 or less when generating electric power;
   a specific surface area of the porous carbon material is 100 m$^2$/g or more as measured by the nitrogen BET method; and a pore volume of the porous carbon material is 0.2 cm³/g or more as measured by the BJH method and 0.1 cm³/g or more as measured by the MP method.

4. The electrode according to claim 1, wherein an oxygen reduction starting potential of the porous carbon material is more noble than 0.15 V as measured versus a Ag/AgCl reference electrode.

5. The electrode according to claim 1, wherein the porous carbon material includes an oxygen reduction catalyst supported thereon, and wherein the plant-derived porous carbon material and the oxygen rejection catalyst each increase a rate of the oxygen reduction.

6. The electrode according to claim 5, wherein the oxygen reduction catalyst is at least one material selected from the group consisting of a noble metal, a transition-metal oxide, a transition-metal porphyrin, phthalocyanine, a porphyrin polymer, a phthalocyanine polymer, perovskite, and a product of pyrolysis of a cobalt salt using polyacrylonitrile.

7. The electrode according to claim 1, wherein the porous carbon material is supported on a supporting member, and wherein the electrode outputs current during the catalysis of the oxygen reduction.

8. The electrode according to claim 1, wherein the electrode is used as a positive electrode of a battery that produces an electric current when the plant-derived porous carbon material catalyzes the oxygen reduction at the electrode.

9. An electrode material comprising a plant-derived porous carbon material that catalyzes oxygen reduction at the electrode material.

10. The electrode material according to claim 9, wherein the porous carbon material is used for oxygen reduction in conjunction with an electrolyte having a pH of 3 or more and 10 or less.

11. The electrode material according to claim 9, wherein:
a specific surface area of the porous carbon material is 100 m²/g or more as measured by the nitrogen BET method; and
a pore volume of the porous carbon material is 0.2 cm³/g or more as measured by the BJH method and 0.1 cm³/g or more as measured by the MP method.

12. The electrode material according to claim 9, wherein an oxygen reduction starting potential of the porous carbon material is more noble than 0.15 V as measured versus a Ag/AgCl reference electrode.

13. A battery comprising a positive electrode including a plant-derived porous carbon material that catalyzes oxygen reduction at the positive electrode.

14. The battery according to claim 13, wherein the porous carbon material is used for oxygen reduction under a pH-neutral condition.

15. The battery according to claim 13, wherein:
a specific surface area of the porous carbon material is 100 m²/g or more as measured by the nitrogen BET method; and
a pore volume of the porous carbon material is 0.2 cm³/g or more as measured by the BJH method and 0.1 cm³/g or more as measured by the MP method.

16. The battery according to claim 13, wherein an oxygen reduction starting potential of the positive electrode is more noble than 0.15 V as measured versus a Ag/AgCl reference electrode.

17. The battery according to claim 13, wherein the battery includes an electrolytic solution containing a buffer substance.

18. The battery according to claim 17, wherein the buffer substance has a $pK_a$ of 4 or more and 10 or less.

19. The battery according to claim 13, wherein the battery is one of an enzymatic biofuel cell and a microbial fuel cell.

* * * * *

UNITED STATES PATENT AND TRADEMARK OFFICE
CERTIFICATE OF CORRECTION

PATENT NO.         : 9,647,305 B2
APPLICATION NO.    : 14/167756
DATED              : May 9, 2017
INVENTOR(S)        : Hironori Iida et al.

It is certified that error appears in the above-identified patent and that said Letters Patent is hereby corrected as shown below:

In the Claims

Claim 5, Column 27, Line 4: REPLACE "oxygen rejection catalyst" with "oxygen reduction catalyst"

Signed and Sealed this
Fourth Day of July, 2017

Joseph Matal
*Performing the Functions and Duties of the*
*Under Secretary of Commerce for Intellectual Property and*
*Director of the United States Patent and Trademark Office*